(12) United States Patent
Chopra et al.

(10) Patent No.: US 11,944,804 B2
(45) Date of Patent: Apr. 2, 2024

(54) SYSTEMS AND METHODS FOR PUMP-ASSISTED BLOOD CIRCULATION

(71) Applicant: CardioDyme, Inc., New York, NY (US)

(72) Inventors: Gopal K. Chopra, New York, NY (US); William Graham, Houston, TX (US); Bryan Lynch, Houston, TX (US); Jeffrey A. LaRose, Raleigh, NC (US)

(73) Assignee: CARDIODYME, INC., New York, NY (US)

( * ) Notice: Subject to any disclaimer, the term of this patent is extended or adjusted under 35 U.S.C. 154(b) by 0 days.

(21) Appl. No.: 18/185,492

(22) Filed: Mar. 17, 2023

(65) Prior Publication Data

US 2023/0218888 A1 Jul. 13, 2023

Related U.S. Application Data

(63) Continuation of application No. 17/853,345, filed on Jun. 29, 2022, now Pat. No. 11,628,294, which is a
(Continued)

(51) Int. Cl.
*A61M 60/117* (2021.01)
*A61M 60/178* (2021.01)
(Continued)

(52) U.S. Cl.
CPC ........ *A61M 60/812* (2021.01); *A61M 60/117* (2021.01); *A61M 60/178* (2021.01);
(Continued)

(58) Field of Classification Search
CPC .............. A61M 60/237; A61M 60/806; A61M 60/117; A61M 60/422; A61M 60/178; A61M 60/818
(Continued)

(56) References Cited

U.S. PATENT DOCUMENTS

| | | | |
|---|---|---|---|
| 5,205,721 A | 4/1993 | Isaacson |
| 5,527,159 A | 6/1996 | Bozeman, Jr. |
| 5,678,306 A | 10/1997 | Bozeman, Jr. |
| 5,692,882 A | 12/1997 | Bozeman, Jr. |
| 5,947,892 A | 9/1999 | Benkowski |

(Continued)

OTHER PUBLICATIONS

International Search Report in PCT/US2021/050925, dated Jan. 3, 2022 (12 pages).

*Primary Examiner* — Erin M Piateski
(74) *Attorney, Agent, or Firm* — Bookoff McAndrews, PLLC

(57) ABSTRACT

Disclosed are systems, devices, and methods that employ a pump to assist or support blood flow. An apparatus for pumping blood may include a pump housing having an outer wall disposed about a longitudinal pump axis, and having an upstream end and a downstream end; a blood flow straightener having a plurality of fins and positioned in the upstream end of the pump housing and secured to the pump housing by the plurality of fins; a diffuser having a plurality of diffuser fins and positioned in the downstream end of the pump housing and secured to the pump housing by the plurality of diffuser fins; and an impeller positioned between the blood flow straightener and the diffuser, and including a plurality of impeller blades. The apparatus may further include a pump drive configured to impart a rotational motion to the impeller by applying a magnetic field.

13 Claims, 19 Drawing Sheets

Related U.S. Application Data continuation of application No. 17/478,344, filed on Sep. 17, 2021, now Pat. No. 11,400,276.

(60) Provisional application No. 63/080,509, filed on Sep. 18, 2020.

(51) Int. Cl.
*A61M 60/237* (2021.01)
*A61M 60/403* (2021.01)
*A61M 60/422* (2021.01)
*A61M 60/806* (2021.01)
*A61M 60/812* (2021.01)
*A61M 60/818* (2021.01)

(52) U.S. Cl.
CPC ........ *A61M 60/237* (2021.01); *A61M 60/403* (2021.01); *A61M 60/422* (2021.01); *A61M 60/806* (2021.01); *A61M 60/818* (2021.01)

(58) Field of Classification Search
USPC .......................................................... 600/16
See application file for complete search history.

(56) References Cited

U.S. PATENT DOCUMENTS

| | | | |
|---|---|---|---|
| 5,957,672 A | 9/1999 | Aber | |
| 6,018,208 A * | 1/2000 | Maher | A61M 60/422 417/423.1 |
| 6,058,958 A | 5/2000 | Benkowski | |
| 6,135,729 A | 10/2000 | Aber | |
| 6,183,412 B1 | 2/2001 | Benkowski | |
| 6,605,032 B2 | 8/2003 | Benkowski | |
| 6,652,447 B2 | 11/2003 | Benkowski | |
| 7,175,588 B2 | 2/2007 | Morello | |
| 7,396,327 B2 | 7/2008 | Morello | |
| 7,856,335 B2 | 12/2010 | Morello | |
| 7,951,062 B2 | 5/2011 | Morello | |
| 8,190,390 B2 | 5/2012 | Morello | |
| 8,303,482 B2 | 11/2012 | Schima | |
| 8,323,173 B2 | 12/2012 | Benkowski | |
| 8,376,926 B2 | 2/2013 | Benkowski | |
| 2009/0041595 A1 | 2/2009 | Garzaniti et al. | |
| 2009/0156885 A1 | 6/2009 | Morello | |
| 2010/0130809 A1 | 5/2010 | Morello | |
| 2015/0335803 A1 | 11/2015 | Yamane | |
| 2016/0199556 A1 | 7/2016 | Ayre | |
| 2018/0228950 A1* | 8/2018 | Janeczek | A61M 60/237 |
| 2019/0321529 A1* | 10/2019 | Korakianitis | A61M 60/422 |

* cited by examiner

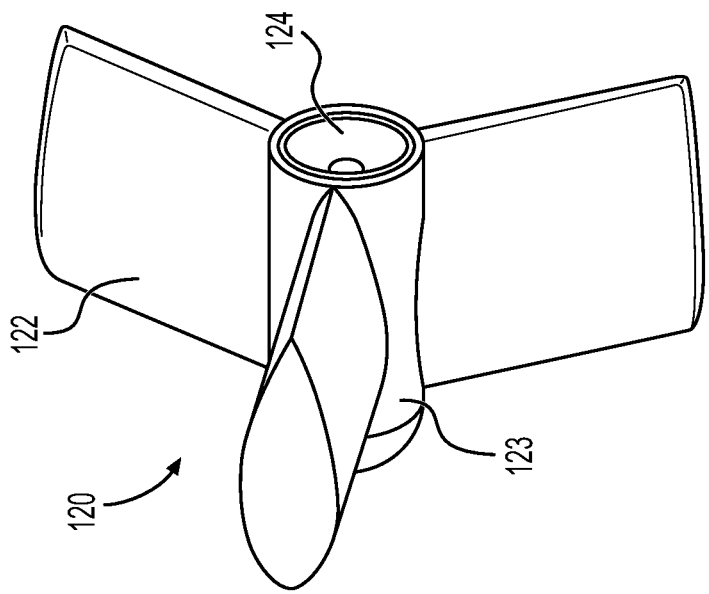
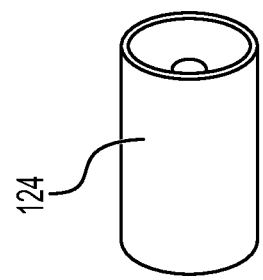
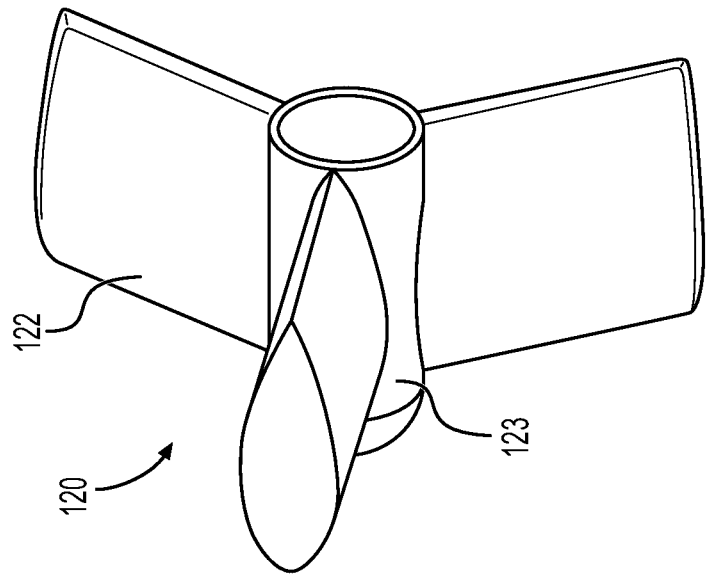
*FIG. 3B*
*FIG. 3A*

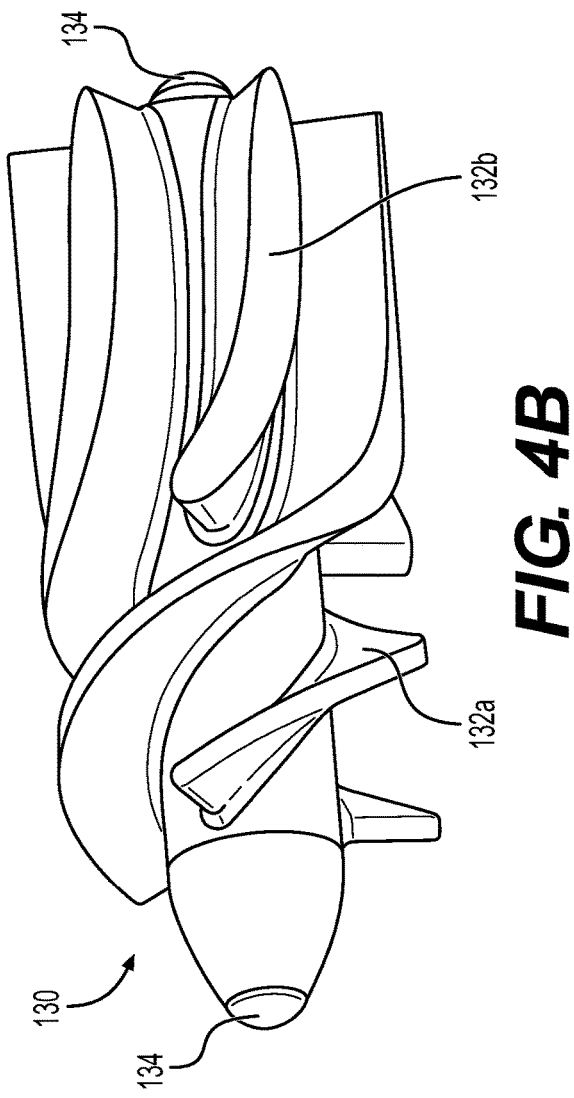
FIG. 4A
FIG. 4B

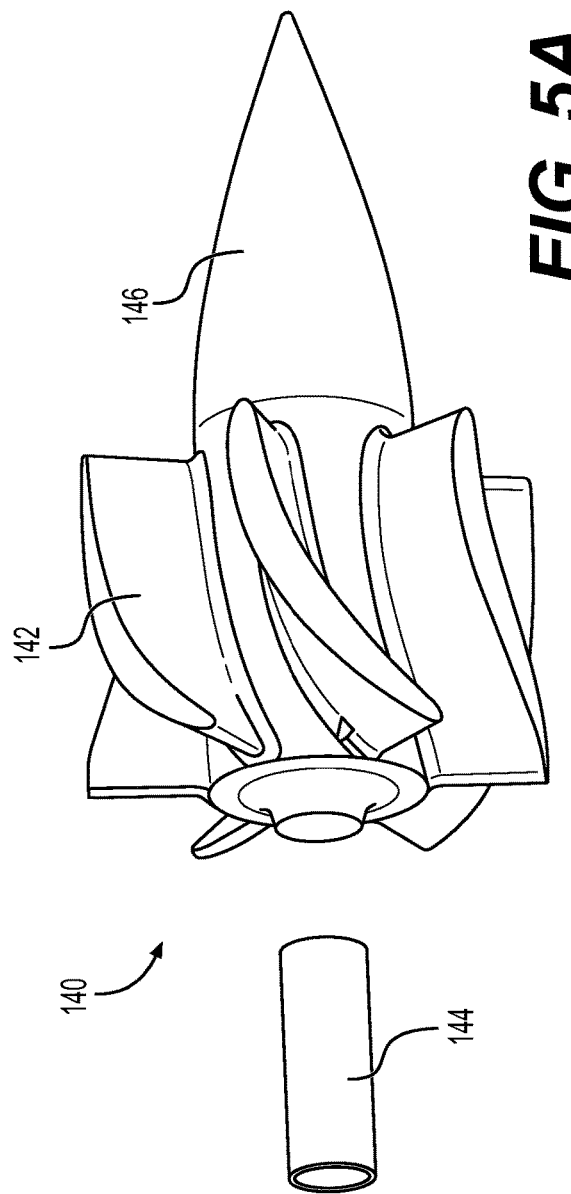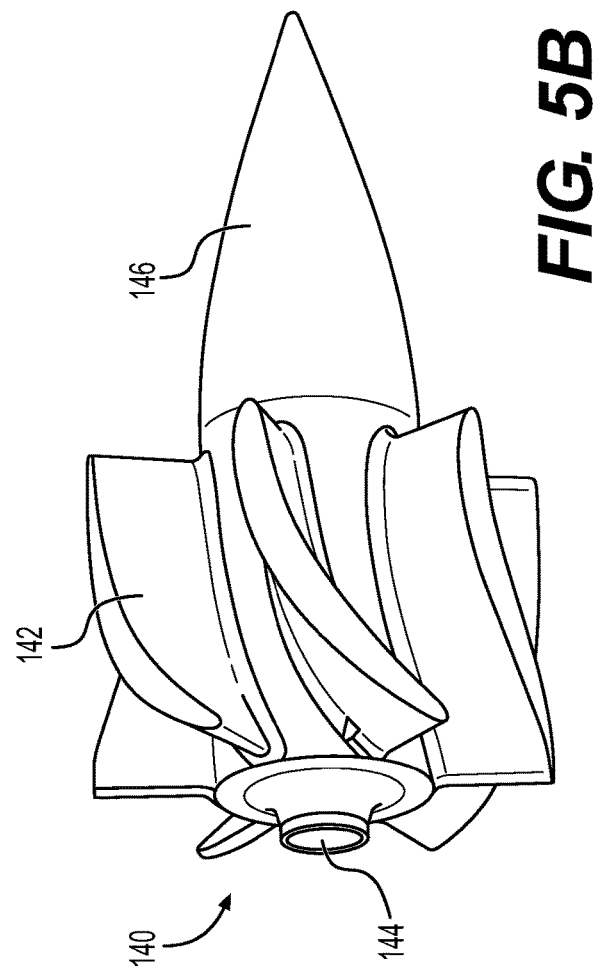

SYSTEMS AND METHODS FOR PUMP-ASSISTED BLOOD CIRCULATION

PRIORITY

This is a continuation of U.S. patent application Ser. No. 17/853,345, filed Jun. 29, 2022, which is a continuation of U.S. patent application Ser. No. 17/478,344, filed Sep. 17, 2021, now U.S. Pat. No. 11,400,276, issued Aug. 2, 2022, which claims the benefit of priority from Provisional Application No. 63/080,509 filed Sep. 18, 2020, which are hereby incorporated herein by reference in their entirety.

TECHNICAL FIELD

Various aspects of the disclosure relate generally to systems and methods for using a pump to assist in blood circulation. According to examples, the disclosure relates to systems, devices, and related methods for use and control of an axial flow pump to provide circulatory assistance or bypass. In embodiments, the pump may be a multi-stage axial flow pump used to circulate blood in intraventricular or extracorporeal applications.

BACKGROUND

In a patient with a heart condition, the heart may have difficulty circulating blood through the patient's body. For example, a patient with heart failure can have insufficient ventricular blood output due to issues with the strength or rhythm of the contraction of one or more chambers of the heart. In other situations, such as surgical or ambulatory settings, it may be necessary to bypass some or all blood flow. In such cases, pumps may be implanted to the heart and vascular system or otherwise connected to the patient's circulatory system to assist or bypass the heart and improve blood flow. Because these pumps are critical to the health and survival of the patient, they must be effective, efficient, and reliable. The present disclosure is directed to methods and systems focused on addressing one or more of these above-referenced challenges or other challenges in the art.

SUMMARY

Aspects of the disclosure relate to, among other things, systems, devices, and methods that employ a pump to assist or support blood flow. In embodiments, an axial-flow pump aids ventricular circulation or provides a partial or complete bypass for blood circulation. Each of the aspects disclosed herein may include one or more of the features described in connection with any of the other disclosed aspects.

For instance, an apparatus for pumping blood may include a pump housing having an outer wall radially disposed about a longitudinal pump axis, the pump housing having an upstream end and a downstream end; a blood flow straightener having a plurality of fins and positioned in the upstream end of the pump housing and secured to the pump housing by the plurality of fins; a diffuser having a plurality of diffuser fins and positioned in the downstream end of the pump housing and secured to the pump housing by the plurality of diffuser fins; and an impeller positioned between the blood flow straightener and the diffuser within the pump housing, the impeller including a plurality of impeller blades. The apparatus may further include a pump drive positioned circumferentially about the impeller and configured to impart a rotational motion to the impeller by applying a magnetic field to the impeller, wherein the impeller is supported by an upstream bearing that cooperates with an upstream bearing mount portion of the blood flow straightener and a downstream bearing that cooperates with a downstream bearing mount portion of the diffuser.

According to the disclosure, an apparatus for pumping blood may include a pump housing having an outer wall radially disposed about a longitudinal pump axis, the pump housing having an upstream end and a downstream end; a blood flow straightener having a plurality of fins and positioned in the upstream end of the pump housing; a diffuser having a plurality of diffuser fins and positioned in the downstream end of the pump housing; an impeller positioned between the blood flow straightener and the diffuser within the pump housing, the impeller including a plurality of impeller blades; and a stator cartridge including a stator housing and a stator core, the stator cartridge removably positioned circumferentially about the pump housing and configured to impart a rotational motion to the impeller by applying a magnetic field to the impeller.

A disclosed apparatus for pumping blood may include a pump housing having an outer wall radially disposed about a longitudinal pump axis, the pump housing having an upstream end, a downstream end, an externally threaded portion between the upstream end and the downstream end, and a flanged portion extending radially outward from the outer wall; a blood flow straightener having a plurality of fins and positioned in the upstream end of the pump housing; and a diffuser having a plurality of diffuser fins and positioned in the downstream end of the pump housing. The disclosed apparatus may further include an impeller positioned between the blood flow straightener and the diffuser within the pump housing, the impeller including a plurality of impeller blades; a pump drive positioned circumferentially about the outer wall and configured to impart a rotational motion to the impeller; and a tube stretcher configured to modify a dimension of the pump housing by being threaded onto the externally threaded portion and abutting the flanged portion.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated herein and constitute a part of this specification, illustrate exemplary aspects of the disclosure and, together with the description, explain the principles of the disclosure.

FIGS. 3A and 3B are perspective views of a flow straightener and front bearing in separate and installed states, respectively, according to aspects of this disclosure;

FIGS. 4A and 4B are front and rear perspective views of an impeller, respectively, according to aspects of this disclosure;

FIGS. 5A and 5B are perspective views of a diffuser and rear bearing in separate and installed states, respectively, according to aspects of this disclosure;

DETAILED DESCRIPTION

Aspects of this disclosure relate to systems and methods for using a multi-stage axial flow pump to circulate blood in intraventricular or extracorporeal applications. An axial flow pump in accordance with the present disclosure may be implanted, at least partially, into a chamber of the heart, such as the right ventricle. In such intraventricular applications, the pump may be a component in a cardiac assist system that aids the heart in circulating blood.

An axial flow pump in accordance with the present disclosure can also be connected to a patient's circulatory system such that the pump remains outside of the patient's body. In these extracorporeal applications, the pump may be a component in a partial or total bypass system that circulates blood from one point of the circulatory system to another point of the circulatory system.

An axial flow pump can also be connected to a patient's circulatory system and be implanted, connected to the circulatory system with implantable connectors and grafts in a manner similar to the ventricular device.

For ease of description, portions of the disclosed devices and/or their components are referred to as upstream and downstream portions. It should be noted that the term "upstream" is intended to refer to portions closer to the source of the blood flow, and the term "downstream" is used herein to refer to portions further away from the source of the blood flow. Further, as used herein, the terms "about," "approximately" and "substantially" indicate a range of values within +/−10% of a stated or implied value. Additionally, terms that indicate the geometric shape of a component/surface refer to exact and approximate shapes.

Figure 1:
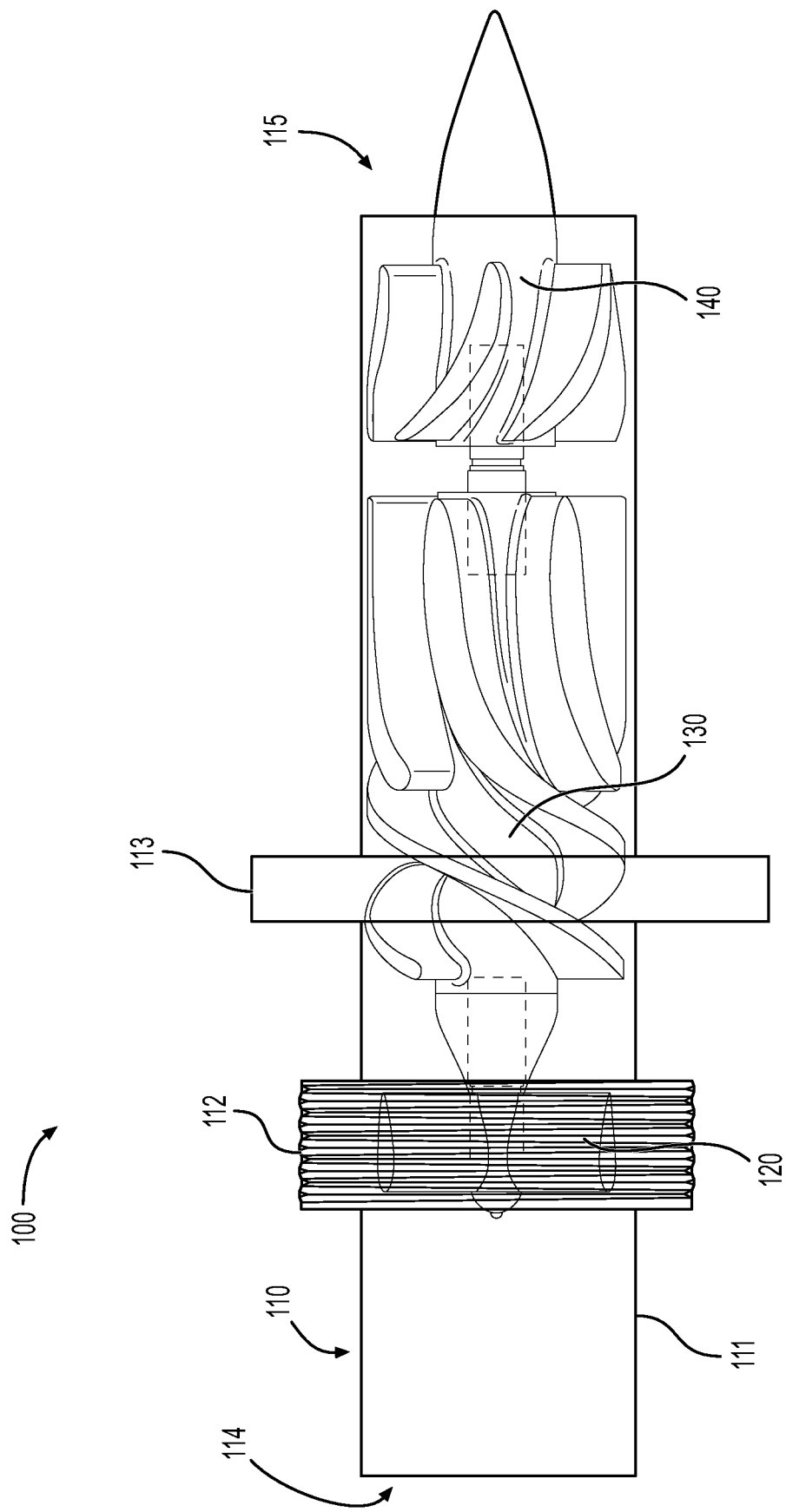
FIG. 1 is a side view of a pump assembly with the housing illustrated as being transparent, according to aspects of this disclosure.

Referring to FIG. 1, a pump assembly 100 in accordance with one or more embodiments of this disclosure is shown. Pump assembly 100 may include a pump housing 110 (illustrated in FIG. 1 as partially transparent) for containing the blood-contacting components of pump assembly 100 and through which blood can be pumped. Pump housing 110 can include a flow tube 111 having a threaded portion 112 and a flanged portion 113 on an outer surface thereof.

Pump housing 110, and specifically flow tube 111, has an opening at an upstream end 114 and another opening at a downstream end 115, with flow tube 111 fluidly connecting upstream end 114 with downstream end 115. Flow tube 111 may have a substantially consistent internal diameter of about 0.5 inches (about 12.5 mm), and may have a generally consistent outer diameter in regions other than the regions of threaded portion 112 and flanged portion 113. Threaded portion 112 may be an externally threaded portion of pump housing 110 configured to engage a tube stretcher 116 (described further below), and flanged portion 113 may protrude radially from flow tube 111 and be abutted by tube stretcher 116. In some embodiments, threaded portion 112 may be upstream of flanged portion 113, and may be positioned in an area adjacent to and radially outside of flow straightener 120. The purpose and function of tube stretcher 116 will be explained below with respect to FIGS. 16 and 17.

The blood-contacting components of pump assembly 100, for example, a flow straightener 120, an impeller 130, and a diffuser 140, may be secured and housed within flow tube 111. These internal components are illustrated with pump housing 110 removed in FIG. 2.

In some embodiments, as blood flows from the upstream end 114 of pump housing 110 to the downstream end 115 of pump housing 110, it can pass through a flow straightener 120 that can also serve as the support for the bearing components that enable the rotation of impeller 130. Flow straightener 120 can be positioned in pump housing 110 and secured by, for example, an interference fit, a welded connection, being integrally formed with pump housing 110, and/or another suitable method. Flow straightener 120 may include, for example, three fins 122, and each can have a teardrop-like cross section, with the narrower pointed end downstream from the leading edge/rounded end. The fins 122 may project radially outward from a central hub 123, and can be equally spaced about the circumference of central hub 123. For example, in embodiments having three fins, the fins may be spaced apart by 120°.

The leading edges of the fins may extend radially from central hub 123 and substantially perpendicular to a central longitudinal axis of the flow straightener. Each fin may have a width in the axial direction of about 0.15 to 0.25 inches (about 4-7 mm). Such a small width is especially suitable for applications where at least a portion of the pump is placed in the right ventricle, so that the pump does not protrude too far into the ventricle. Each fin may have a length in the radial direction that is selected to extend from the central hub to the inner wall of flow tube 111. Providing flow straightener 120 with an outer diameter substantially equal to the inner diameter of the flow tube can allow the flow straightener to be press fit into place, and may prevent flow between the ends of fins 122 and pump housing 110.

As illustrated in FIGS. 3A and 3B, flow straightener 120 may have a bearing mount 124 inserted into an opening on the downstream side of the central hub. Bearing mount 124 can include a bearing surface that cooperates with a bearing in the impeller. Front bearing mount 124 can support rotating impeller 130 on a bearing 134 located in the upstream end of impeller 130 and rotating with impeller 130, while still permitting smooth flow through pump housing 110.

The leading edge design discussed above, the fin dimensions, and the distance between the downstream edge of fins 122 and the leading edges of blades of impeller 130 may be especially advantageous to limit turbulence of incoming flow, and reduce stagnation of blood within the pump. Although flow straightener 120 is shown and described with three symmetrically arranged, identically shaped and sized fins 122, embodiments of the disclosure include flow straighteners 120 with more or less than three fins 122, fins 122 that are asymmetrically arranged about hub 123, and fins 122 of varying shapes and sizes. In some embodiments, the axial length of flow straightener 120 and fins 122 may be reduced to a length suitable for the desired specifications of bearing mount 124.

As the blood flow passes flow straightener 120, it then encounters impeller 130. Impeller 130 can be driven to move blood through the flow tube, and to help with durability and reliability of pump assembly 100, impeller 130 (including blades 132 and bearings 134) may be the only moving part in pump housing 110. FIGS. 4A and 4B show front and rear perspective views, respectively, of an impeller in accordance with an embodiment of the present disclosure. Impeller 130 can include a plurality of impeller blades 132, for example, six blades, that protrude from a central portion of impeller 130. Impeller 130 can have bearings 134 inserted into, and extend from, openings located in the middle of the upstream and downstream sides. Bearings 134 can rotate within upstream bearing mount 124 and downstream bearing mount 144 to reduce friction, while permitting smooth blood flow through pump housing 110.

In some embodiments, some impeller blades 132a can wind helically about the central portion of impeller 130 along a substantial portion of the length of impeller 130, while arcuate other blades 132b may be arcuately formed about the central portion of impeller 130 along a portion of the length of impeller 130 that is shorter than the substantial portion of the length that the helical blades 132 extend. In some embodiments, the helically wound blades 132a have a pitch that varies along the axial length of impeller 130 such that the pitch of helically wound blades 132a in an upstream portion of impeller 130 is less than the pitch in a downstream portion of impeller 130. Arcuate blades 132b may be interspersed between helically wound blades 132a (e.g. alternate circumferentially with blades 132a), begin (have a leading edge) in the central portion of impeller 130, and have an initial arc shape that flattens out (becoming essentially linear) as arcuate blades 132b approach the downstream end of impeller 130. Impeller blades 132, including both helically wound blades 132a and arcuate blades 132b, may run substantially parallel to one another and be equally spaced about impeller 130 at the downstream end thereof.

Impeller 130 can spin from about 5,000 to about 15,000 rpm and can generate about 1-6 L/min of blood flow, depending upon variables such as bypass circuit tubing blood flow resistance. The specific geometry of impeller 130 and impeller blades 132 can impact the flow conditions and efficiencies of pump assembly 100. For example, as the flow approaches impeller 130, the shape and angle of the leading edges of impeller blades 132 can cause areas of flow separation and/or flow reversal. Flow separation and flow reversal are conditions that may be capable of damaging the blood cells in the flow and/or creating conditions that can cause an accumulation of thrombus in pump assembly 100. In some applications, flattening and/or rounding of the leading edge of impeller blades 132 can aid in avoiding these conditions.

Further, in some embodiments, the axial length and angle of the impeller blades can be adjusted to improve flow characteristics for different circulatory pressure and flow applications. For example, providing a longer impeller 130 can improve flow conditions when a high flow at a high pressure is indicated, and an impeller 130 having blades 132 positioned at a steeper angle can improve flow conditions for applications calling for a lower flow at a high pressure. In some embodiments, as discussed below with respect to FIG. 19, the flow and pressure requirements may be met using multiple stages of impeller/diffuser pairs.

As the blood passes impeller 130, the flow approaches a diffuser 140 positioned at the downstream end of impeller 130 to improve flow characteristics prior to exiting pump housing 110.

In some embodiments, flow straightener 120 and diffuser 140 may be stationary components that can serve as the upstream and downstream bearing mounts 124, 144, as reducing the number of moving parts can aid in reliability, manufacturability, and system efficiency. In such embodiments, impeller 130 (including blades 132 and bearings 134) may be the only moving pump component.

As depicted in FIGS. 5A and 5B, diffuser 140 may have a bearing mount 144 inserted into an opening on its upstream side. Bearing mount 144 can include a bearing surface that cooperates with a bearing in the impeller. Bearing mount 144 may be of sufficient diameter and surface area to improve flow characteristics by reducing regions of potential flow stagnation or reversal. Further aiding in improving flow characteristics and reducing flow reversal, diffuser 140 can have an end cap 146 connected to or formed from its downstream end. End cap 146 may be conical in shape and may gradually taper in circumference to a pointed end such that the flow is able to exit diffuser 140 smoothly and with reduced turbulence. In some embodiments, the downstream end of end cap 146 may protrude from pump housing 110, including flow tube 111, which may allow flow tube 111 to be made shorter, reducing manufacturing cost.

Figure 2:
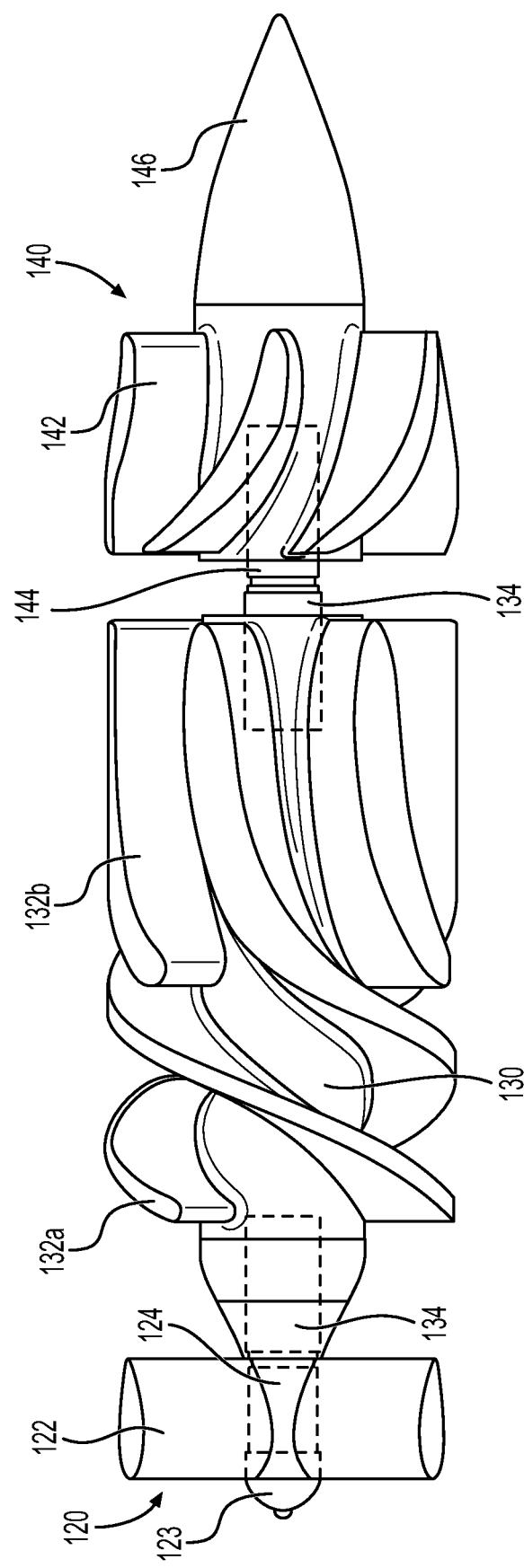
FIG. 2 is a side view of the internal components of a pump assembly, according to aspects of this disclosure.

Diffuser 140 may include diffuser fins 142 to convert the rotational velocity of the flow, imparted by impeller 130, into axial velocity and pump outflow. To this end, diffuser fins 142 can be provided with a curvature configured to gradually arrest the rotation of the flow as it exits impeller 130. For example, diffuser fins 142 may be curved, from their leading edges to their trailing edges, in the direction of the rotation of impeller 130, opposite to the helical curvature of the impeller blades 132, and have a curve that begins with a steeper angle relative to the central axis that approaches being parallel to the central axis at the downstream end of diffuser 140. The concave, axially extending surfaces of fins 142 face a direction opposite to the direction that the concave, axially extending surfaces of blades 132 face, as shown in FIG. 2. In addition, the embodiment shown in FIG. 2 includes only fins 142 having the same axial length.

The configuration of fins 142 (including their spacing and shape) may allow the stationary diffuser fins 142 to be contacted by the rotating flow exiting impeller 130 and gradually redirect that flow such that the flow exiting diffuser 140 has a velocity that has an increased axial component relative to the flow entering diffuser 140.

In some embodiments, providing diffuser 140 with a different number of fins (e.g., one more or one less) than impeller 130 has blades may improve the pump assembly's resistance to thrombosis while not sacrificing performance.

Diffuser 140 can also include end cap 146 to improve the flow characteristics as the blood exits pump assembly 100. End cap 146 may reduce flow reversal and provide a smoother exit flow.

The flow conditions in the transition between impeller 130 and diffuser 140 can be impacted by the shape and size of the cavity between impeller 130 and diffuser 140. Reductions in the volume of the cavity between the downstream end of impeller 130 and the upstream end of diffuser 140, for example, by moving diffuser 140 upstream towards impeller 130, can reduce flow separation and/or flow reversal in the flow. Not only can such a reduction improve the flow through the cavity, but it can also reduce the stress on impeller 130 and bearings 134 that can be caused by an area of increased pressure at the downstream end of impeller 130 due to flow stagnation. A larger axial stress on these components can increase the friction losses in bearings 134 and therefore can lead to higher temperatures. Temperature increases in pump assembly 100 could result in blood coagulation and thrombus formation. Therefore, reductions of the volume of the cavity between impeller 130 and diffuser 140, and the corresponding reductions in the axial forces on impeller 130, can help pump assembly 100 operate more efficiently, and with less damage to the blood flow.

Figure 6:
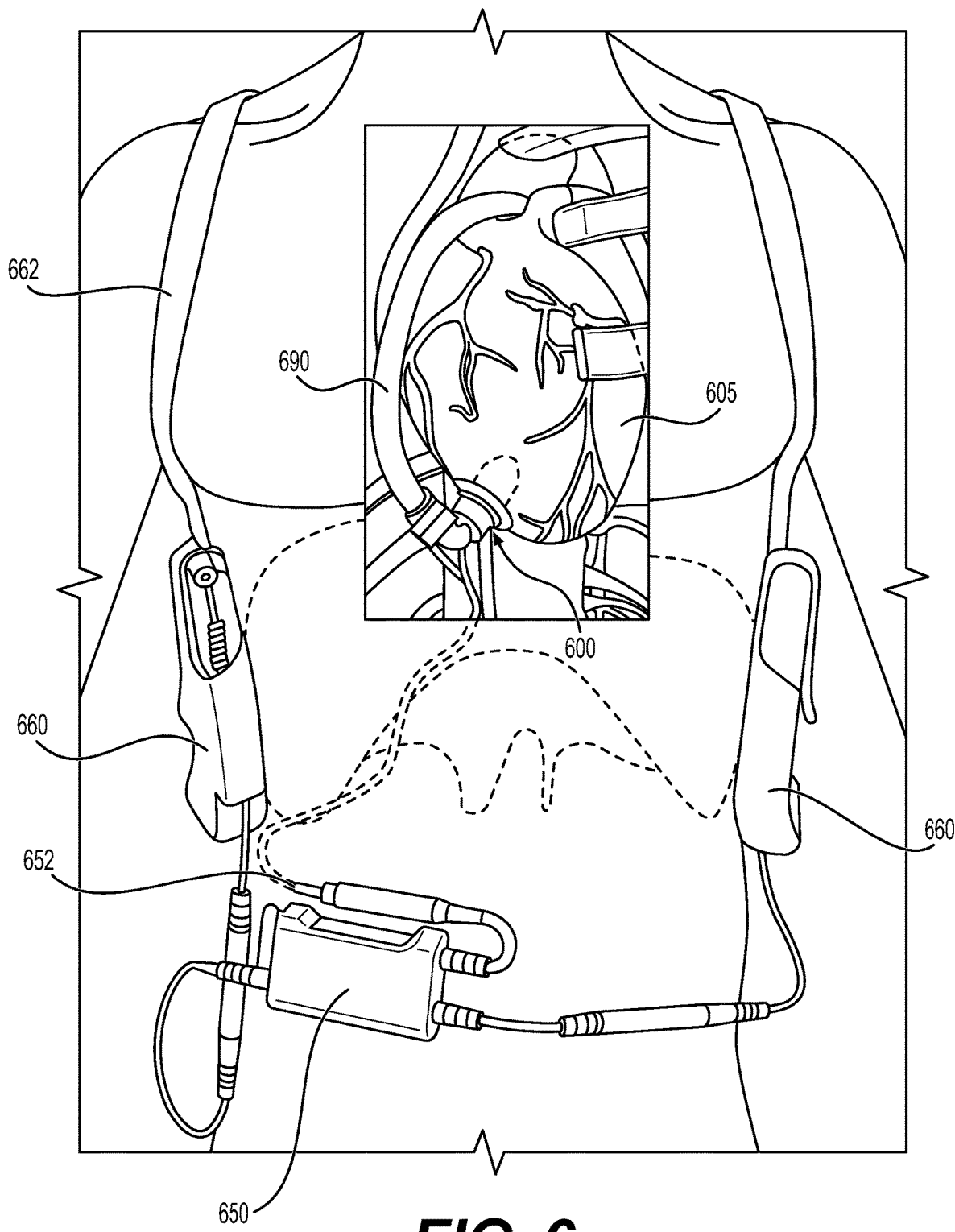
FIG. 6 is an illustration of a pump assembly configured for intraventricular application, according to aspects of this disclosure.

According to an embodiment of this disclosure, depicted in FIG. 6, a pump assembly 600 is deployed to assist a chamber of heart 605. For example, pump assembly 600 can be positioned in the right ventricle of heart 605 to aid heart 605 in delivering blood to another site in the circulatory system of a patient. Although this disclosure describes an embodiment for assisting a right ventricle of a heart 605 in delivering blood to a pulmonary artery, the disclosure is not limited to such use. Aspects of the disclosure may also be used for delivering blood from any other heart chamber (i.e., left ventricle, right atrium, or left atrium) to another portion of the circulatory system (e.g. an artery, vein, or other heart chamber).

Figure 7:
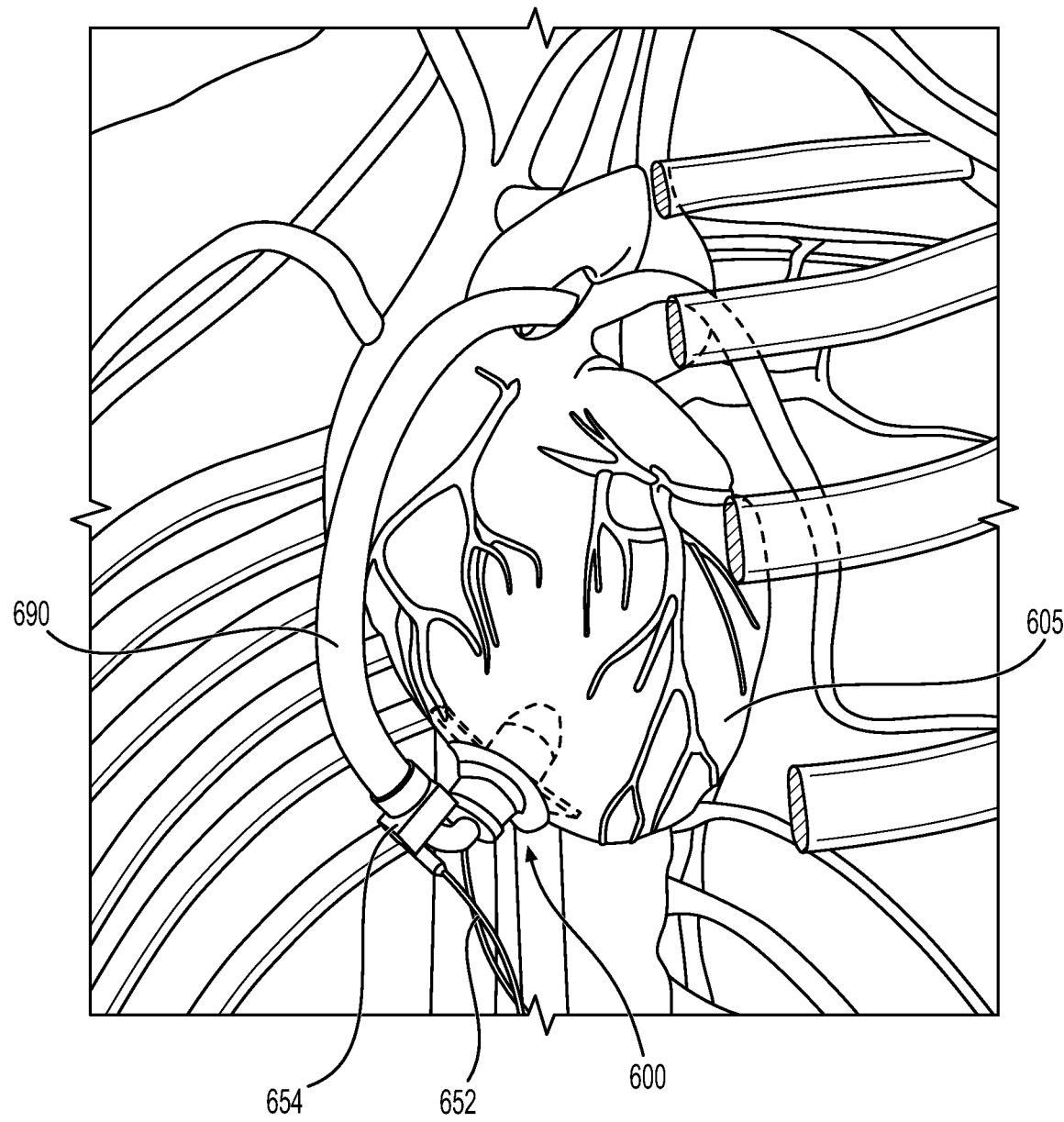
FIG. 7 is a front view of an installed intraventricular pump assembly, according to aspects of this disclosure.

FIGS. 6 and 7 show pump assembly 100 in an installed position in heart 605 and connected to additional components of an apparatus for pumping blood. For example, in order to provide control signals and to monitor the operation of pump assembly 600, a controller 650 can connect by a percutaneous cable 652 and/or wirelessly to pump assembly 600. In applications that can benefit from portability, such as when the patient is ambulatory, controller 650 may be powered by one or more batteries 660 associated with a patient, such as via a body attachment 662. Body attachment 662 may be a holster, belt, or other manner of allowing batteries 660 to be detachably supported by or on the patient's body. In applications that would not benefit from portability, power may be supplied by another suitable method, such as a power supply that plugs into an outlet. In some embodiments, power to some elements of the system can be provided by a direct connection to wall power, and one or more rechargeable batteries may be used to prevent power disruption during outages or during patient transport.

Figure 8:
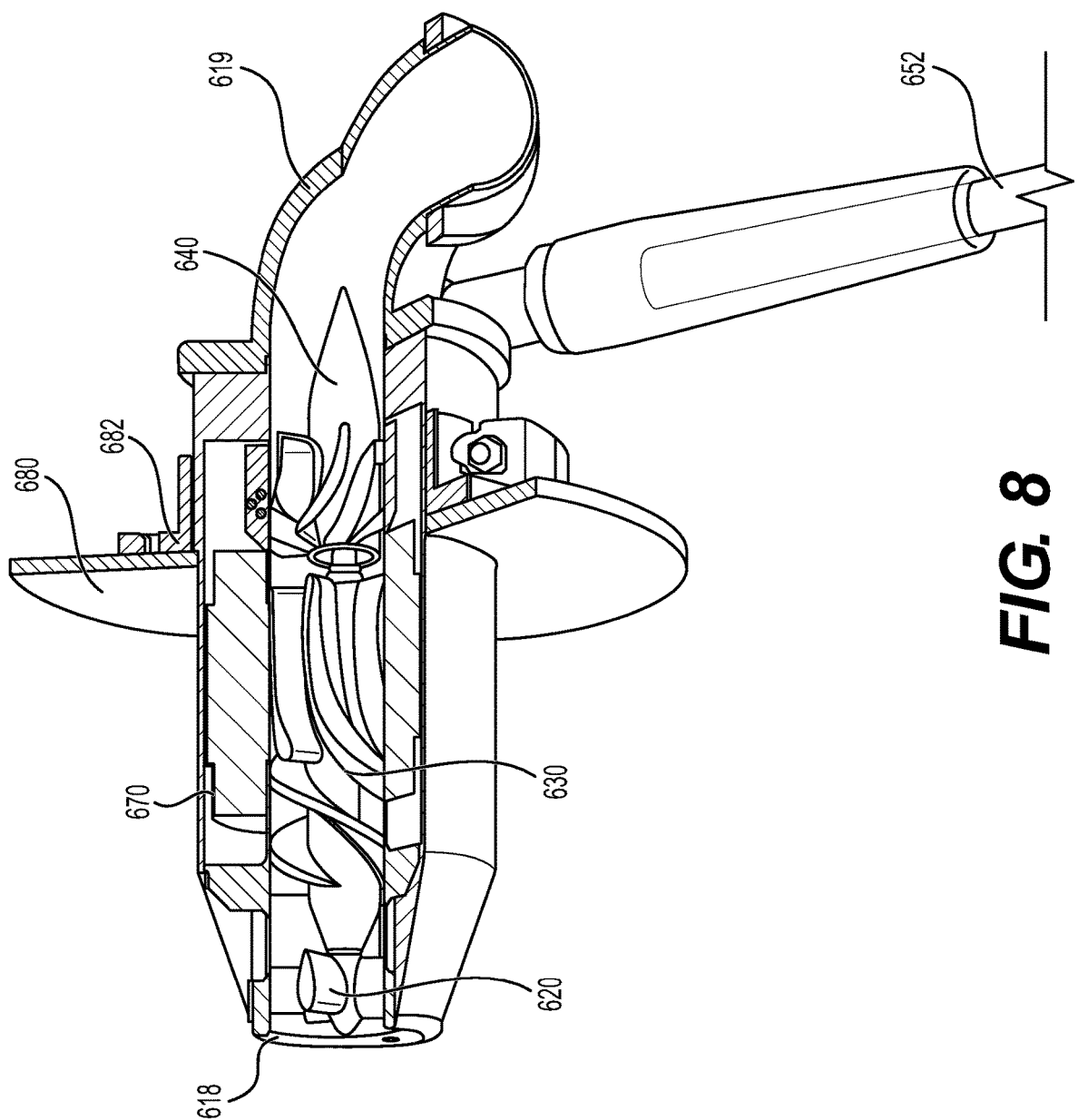
FIG. 8 is a perspective partial cross-sectional view of a pump assembly configured for intraventricular application, according to aspects of this disclosure.
Figure 9:
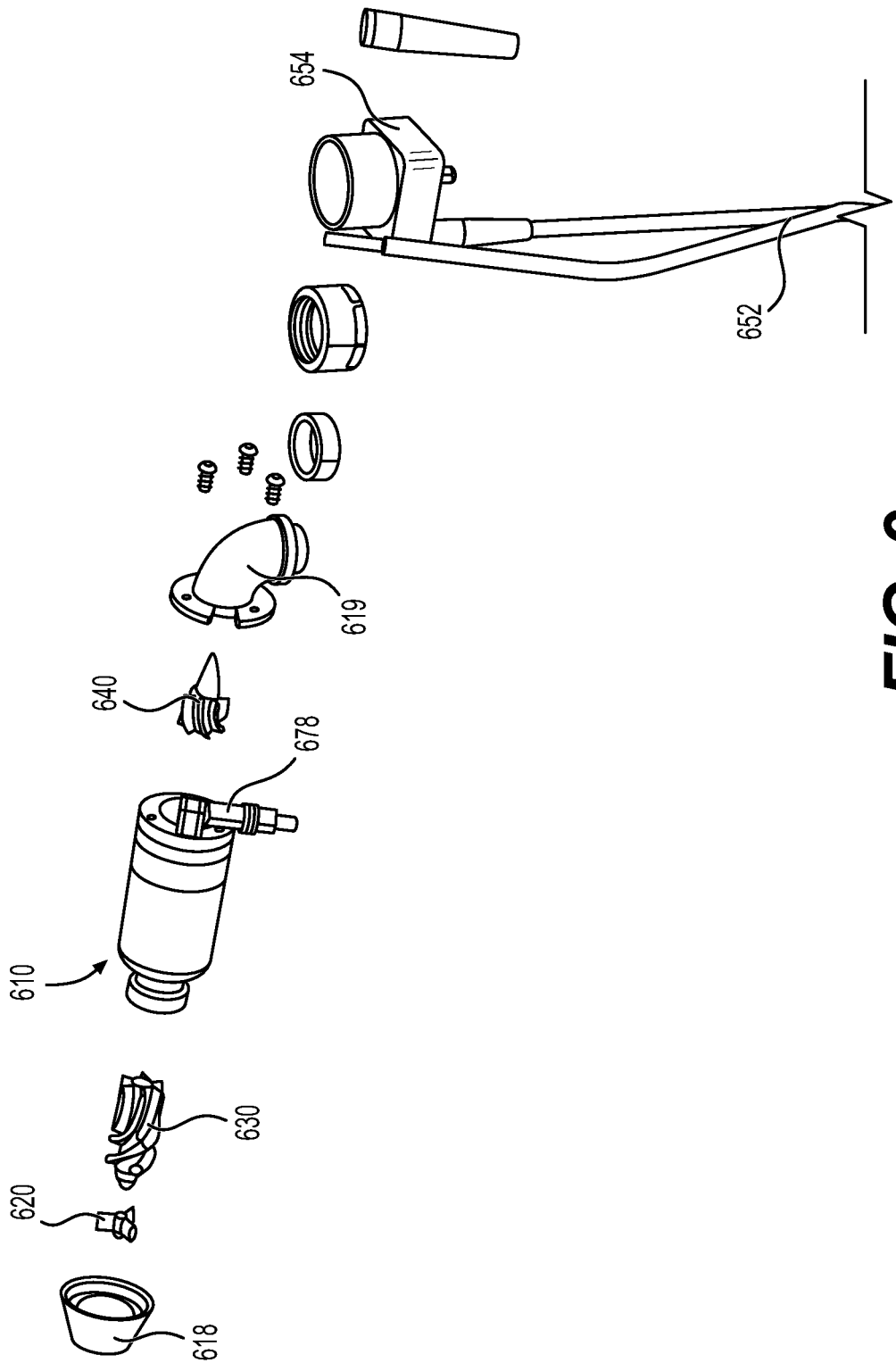
FIG. 9 is an exploded perspective view of the pump assembly of FIG. 8, according to aspects of this disclosure.

Pump assembly 600, shown in FIG. 8 and in an exploded view in FIG. 9, can be a rotary axial-flow mechanical ventricular assist pump including flow straightener 620, impeller 630, and diffuser 640, and may be implanted into, for example, the right ventricle of the heart of a patient. When implanted into a patient's right ventricle, at least a portion of pump assembly 600 can be positioned directly inside the ventricle and can draw blood from the ventricle via an inlet adapter 618 (e.g. an inflow cannula) of pump housing 610. The inlet adapter 618 may include a smooth conical tip for ease of insertion into the ventricle. Inlet adapter 618, and pump housing 610 generally, may be made from a suitable biocompatible material (such as titanium) having a finish, such as a sintered finish, that allows inlet adapter 618 and pump housing 610 to be well integrated to the body environment. The combination of material choice and finish can help enable appropriate tissue growth, while discouraging tissue entrapment into pump assembly 600.

Pump assembly 600 can include a stator 670. A stator 670 can include a non-magnetic stator housing 672 and a stator core 674. Stator 670, in combination with magnetic components of impeller 630, form the pump drive system. Stator 670 is the stationary part of the pump drive system and may be made up of electromagnetic components to produce a rotating magnetic field that magnetically couples to the permanent magnet(s) contained within impeller 630. Stator core 674 can include wire stator coils and ferromagnetic material connected for a traditional motor configuration. The drive circuitry to produce the electrical signals creating the rotating magnetic field may be contained within stator housing 672 or in a separate electronic instrument.

In some embodiments, impeller blades 632 can be formed with or provided with hermetically sealed magnets in each impeller blade 632. In some embodiments, impeller blades 632 may be formed about a single, rod-like core magnet positioned at an axial center of impeller 630. This can be a single, two pole magnet or an assembly of four radially magnetized quadrants for a four-pole configuration which may be more powerful and space-efficient. Whichever arrangement of magnets is employed, the magnets can allow impeller 630 to be driven by the brushless, direct current (DC) stator 670.

In some embodiments, the pump drive system may be a reluctance motor, and rather than having a magnetic component, impeller 630 may be made from a ferrous material such as iron or steel that has been coated with a biocompatible bearing material. Rather than providing impeller 630 with permanent magnets, a reluctance motor can cause non-permanent magnetic poles to be induced in impeller 630.

Depending on the location and polarity of the magnet(s) and or ferrous core used in impeller 630, stator core 674 can be aligned such that the magnetic fields generated by stator core 674 are able to drive impeller 630.

Figure 10:
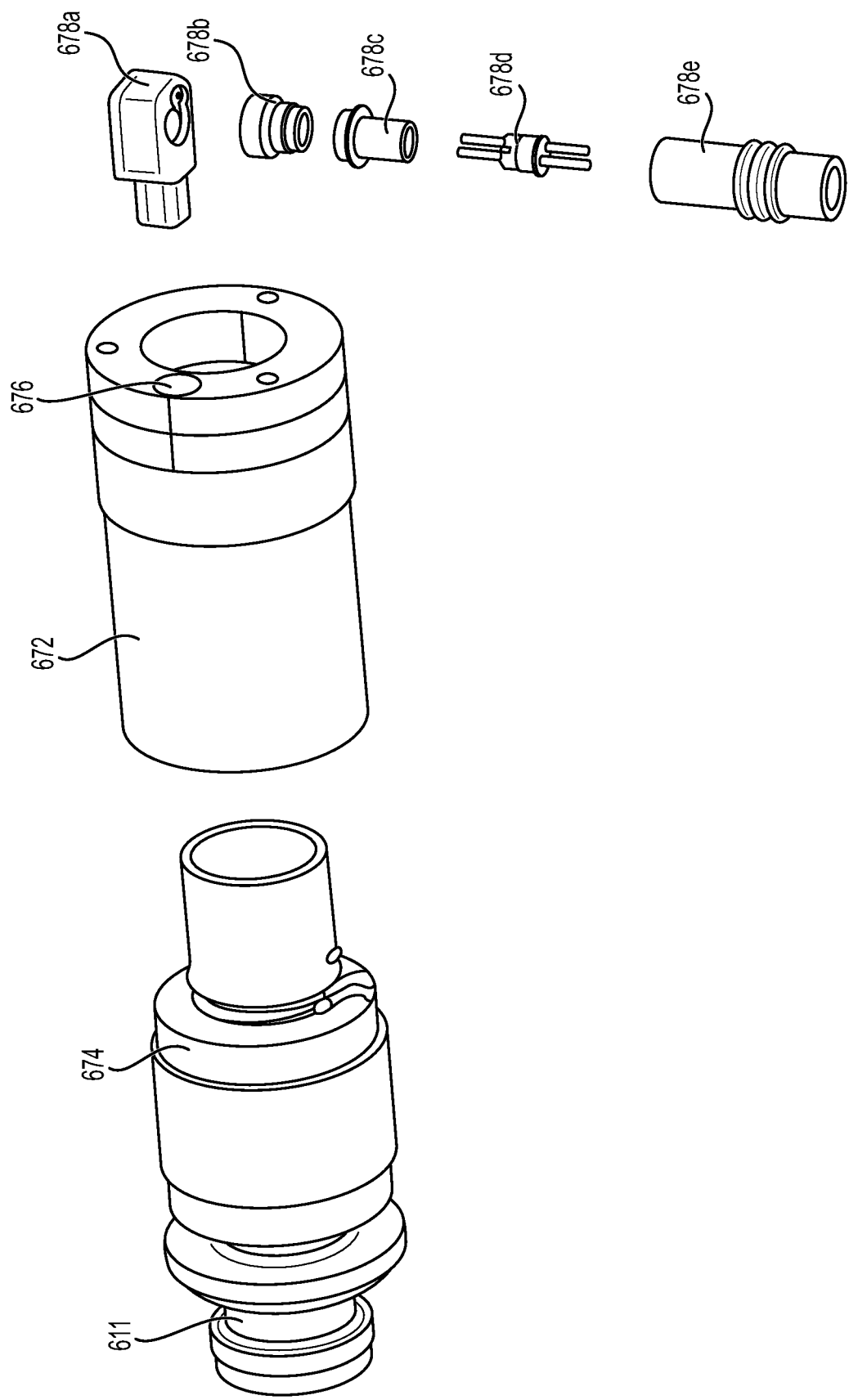
FIG. 10 is an exploded perspective view of the pump housing of FIG. 8, according to aspects of this disclosure.
Figure 11:
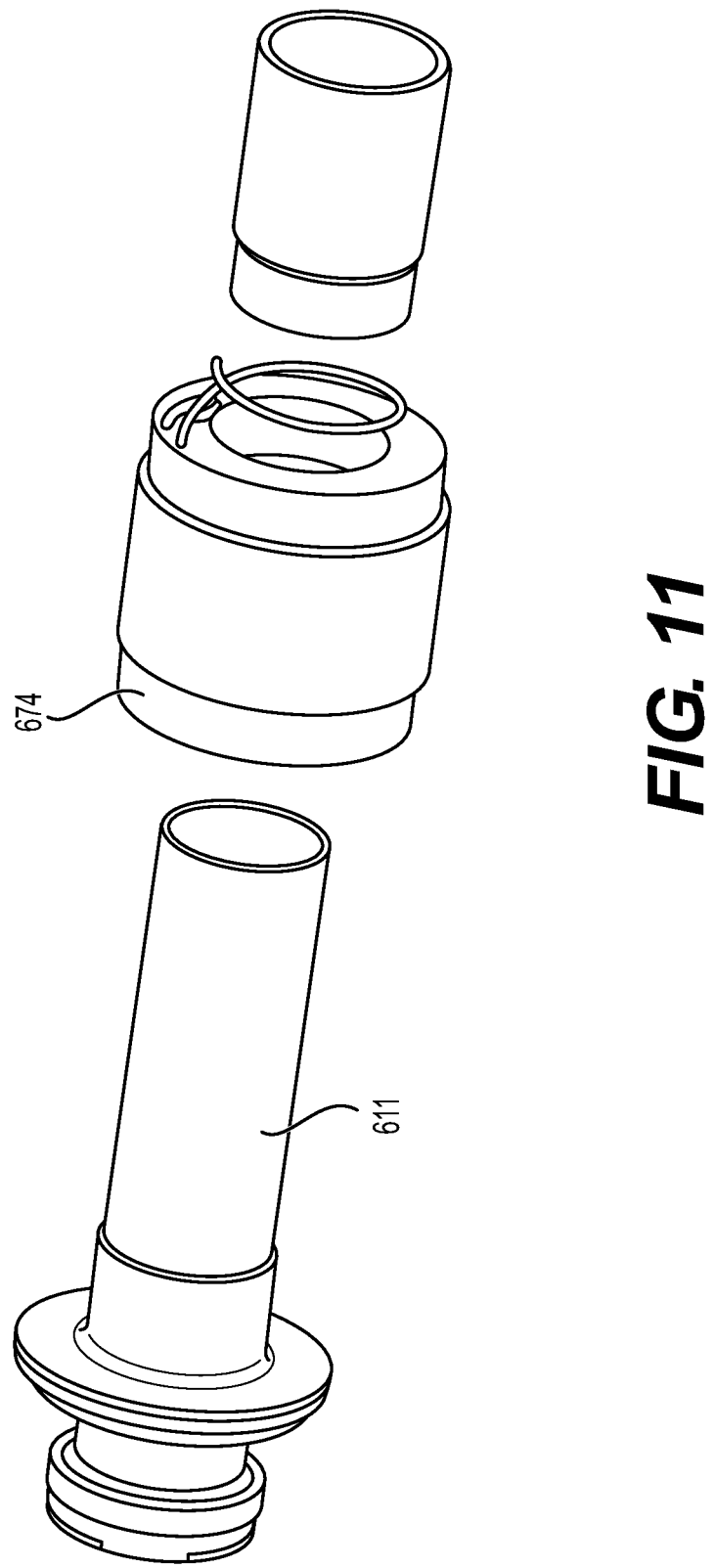
FIG. 11 an exploded perspective view of the flow tube of FIG. 8, according to aspects of this disclosure.

FIG. 10 shows flow tube 611 and stator core 674 with stator housing 672 removed, and FIG. 11 shows flow tube 611 with stator core 674 removed. The cables and wires that provide power and/or signal to stator 670 may exit stator housing 672 through an aperture 676 and connect to feed through 678, for example on a downstream end of stator housing 672. Feed through 678 can allow the cables and wires to pass through pump housing 610 while preserving the hermetic seal that prevents the infiltration of blood or other bodily fluids into the electronic components of pump assembly 600. Feed through 678 can be integrally formed or made up of multiple components, for example, feed through standoff 678a can allow the wires to be exit from the pump housing 610 at a 90 degree angle, feed through port 678b can facilitate a hermetic junction between standoff 678a and feed through cover 678d, hermetic feed through 678c and feed through end piece 678e can allow a casing for the wires to seal to the pump housing. In some embodiments, stator housing 672 may be generally cylindrical in shape, and may circumscribe stator core 674 and abut and/or connect to portions of flow tube 611 and/or pump housing 610.

Returning to FIG. 8, in order to secure pump assembly 600 in place, a flexible cloth or polymer fixation ring 680 may be placed over the right ventricular insertion point to which an adapter ring 682 may then be connected. Fixation ring 680 can be a disk-like element having a central opening through which pump assembly 600 may be partially or completely passed. Fixation ring 680 can be secured to the muscle wall by a suitable method, such as suturing or grafting. Adapter ring 682 may have a cylindrical base with a flanged portion at an upstream side thereof to allow it to be stitched, adhered, or otherwise bonded to fixation ring 680. Because the right ventricular wall is thinner than other portions of the cardiac wall, for example, the left ventricular wall, the ring graft may be double-layered for greater tissue capture and tissue protection.

Pump assembly 600 can be slid into a fixed position via a perforation in the center of fixation ring 680. The depth of insertion may be adjusted based on dimensions of the heart, such as a width of the right ventricle and distance from structures such as valves, which may be located using imaging or feel. The position of pump assembly 600 can be maintained by virtue of locking to adapter ring 682 with a ratcheted screw locking mechanism or other suitable mechanism for securing a position of pump assembly 600 relative to adapter ring 682.

Pump assembly 600 of the cardiac assist device can have an outlet adapter 619 which can be, for example, a cannula having a 90° outflow elbow. Outlet adapter 619 can include an upstream end connected to the pump and a downstream end for connection to a vascular graft 690, using suitable hardware components. In some embodiments, the upstream end of outlet adapter 619 can include a flanged portion that couples to a downstream portion of pump housing 610. In some embodiments, the direction that the downstream end of outlet adapter 619 faces can be adjustable. For example, outlet adapter 619 can be flexible (e.g., as a result of material properties, or in an accordion-like fashion like a drinking straw) to allow the downstream end to move relative to the upstream end. This construction may assist in the implantation procedure.

A flow monitoring or other physiologic monitoring system may be included in outlet adapter 619, in vascular graft 690, or another suitable point along the blood flow path. For example, as illustrated in FIGS. 6, 7, and 9, a flow probe 654 may be placed between the downstream end of outlet adapter 619 and vascular graft 690. In the event that removal or replacement of flow probe 654 becomes necessary or desired, the placement of flow probe 654 may allow the removal/replacement to be carried out without the need to dissect or displace the arterial trunk.

The flow monitoring system can be employed to continuously monitor graft blood flow. Flow probe 654 may be, for example, a direct flow measurement sensor, such as an ultrasonic flow sensor that does not require contact with the blood to accurately measure flow. The ultrasonic flow probe can be employed to measure flow rate and pulsatility characteristics of the blood flow in real time. This information can be passed to the controller 650 and/or a physician control interface. Real-time data from the flow probe can be factored into decisions made by the physician or control software to aid in pump impeller speed control or other control aspects of the system. In some embodiments, the flow monitoring system may estimate the flow by performing calculations based on pump operating parameters, pressure measurements, and the like. Other physiologic sensors may be incorporated into the device and/or system, such as blood pressure, body temperature, pulse oximetry, and/or ECG sensors, for example. The flow monitoring system or other monitor may be deployed directly on outlet adapter 619 or another position downstream therefrom.

The flow monitoring data from pump and sensors including flow and pressure can be incorporated into a feedback loop to adjust either manually or automatically the pump settings to improve flow and physiological condition of the patient or to avert an adverse event from occurring or worsening as the system detects it. This can allow pump assembly 600 to be responsive based on flow and circuit inputs. Pump assembly 600 may cycle speed and thus adjust flow as it relates to pressure based on: time, pulse, monitor data or algorithmic derivatives of that data (via feedback loop-automated or manual alert), and may also be responsive to clinical parameters and physiologic detected events that are clinical or subclinical.

To protect exposed portions of vascular graft 690, a tubular graft protector may be installed over all of vascular graft 690 or any exposed portion of thereof, and the downstream end of vascular graft 190 can be anastomosed to the pulmonary trunk using a vascular anastomosis sewing technique, or other suitable technique. The graft protector may provide external support to help avoid graft pressure compression from neighboring chest wall anatomy, thereby assisting to maintain graft luminal patency. The graft protector may directly connect to adapter 619 or the downstream end of flow probe 654 to encase the upstream end of vascular graft 190. The graft protector can be cut to a customizable length to manage connection points and length of graft.

Cables and wires from the sensors, pump motor and other components may be combined in percutaneous cable 652 and configured to have an adjustable angle of take off from the downstream end of pump assembly 600 so as to accommodate positioning of pump assembly 600 in a position capable of reducing strain on percutaneous cable 652. This can be done with a flexible, pliable, yet firm, and somewhat fixable, take off joint or be on a swivel that can be fixed or left free. This may reduce strain on the cables and wires as well as reducing shear on anatomical organs that may perforate with excessive rubbing from mobility due to breathing, heart beating, or positional strain.

Figure 12:
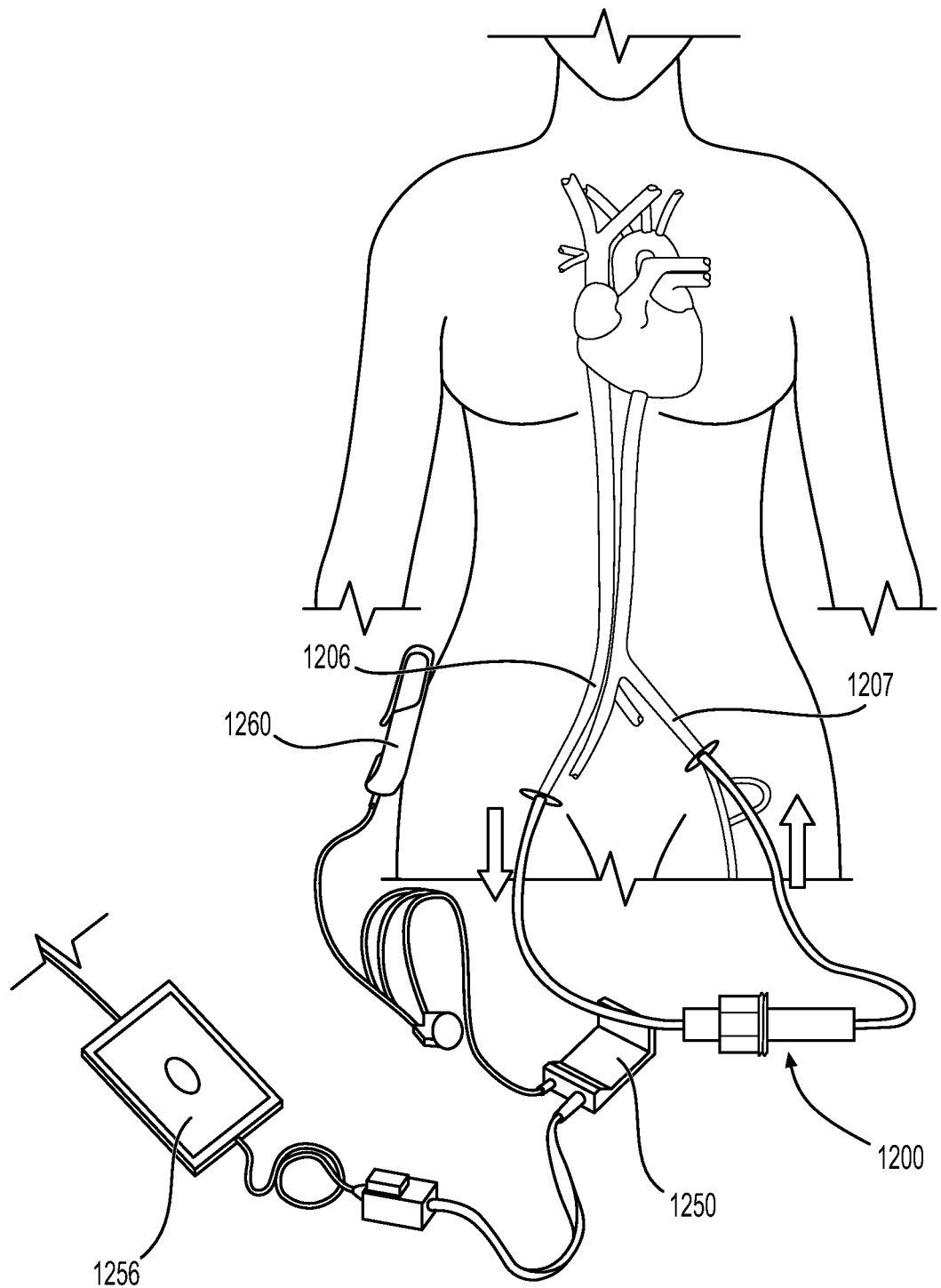
FIG. 12 is an illustration of a pump assembly configured for extracorporeal application, according to aspects of this disclosure.
Figure 13:
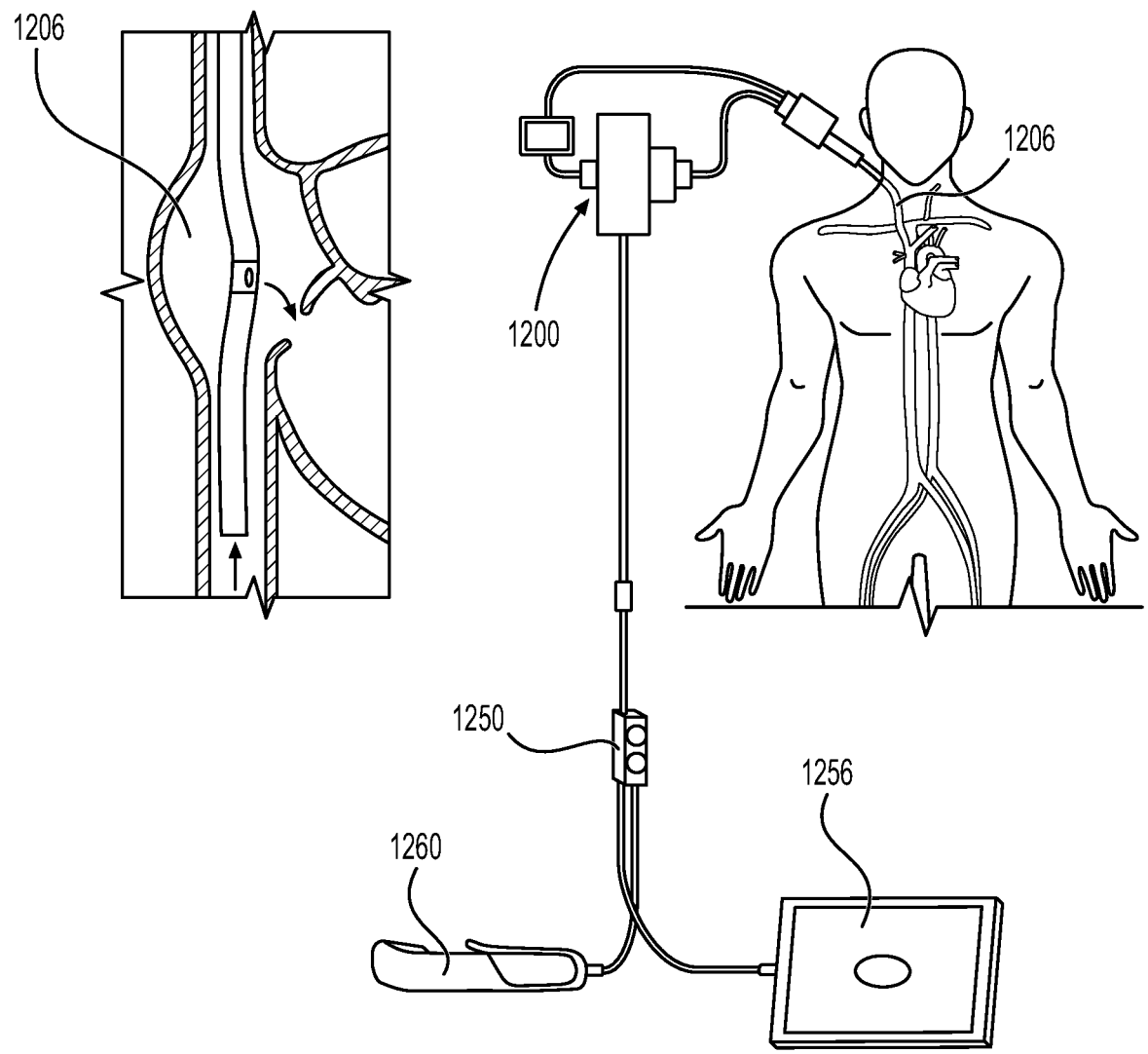
FIG. 13 is an illustration of a pump assembly configured for an alternative extracorporeal application, according to aspects of this disclosure.

FIGS. 12 and 13 are illustrations of pump assembly 1200 and supporting components configured to circulate blood from one point of the circulatory system to another point of the circulatory system in an extracorporeal application. For example, in FIG. 12, an embodiment of this disclosure includes a system that uses pump assembly 1200 to remove blood from a vein 1206 and circulate that blood to an artery 1207, and in FIG. 13, an embodiment of this disclosure includes a system that uses pump assembly 1200 to remove blood from a vein 1206 and circulate that blood to different location in the vein 1206. The disclosure is not limited to such uses, however. Aspects of the disclosure may be used for delivering blood from any blood vessel (e.g. venous or arterial) to any other blood vessel (e.g. venous or arterial). As discussed above, the bypass system pump may be an axial flow blood pump assembly 1200 that can circulate blood through an extracorporeal circuit. Pump assembly 1200 may be used as an extracorporeal circulatory support system for procedures such as those requiring partial cardiopulmonary bypass (e.g. valvuloplasty, mitral valve reoperation, surgery of the vena cava and/or aorta, liver transplant, etc.).

A bypass pump system in accordance with the present disclosure can include a rotary axial-flow mechanical blood pump assembly 1200, controller 1250, one or more batteries 1260, and a physician control interface 1256 to provide extracorporeal circulatory support. Such a system may be used, for example, during procedures not requiring complete cardiopulmonary bypass (e.g. valvuloplasty, mitral valve reoperation, surgery of the vena cava and/or aorta, liver transplant, etc.).

In both ventricular and extracorporeal applications, physician control interface 1256, such as an external console, can be connected (via a wired or wireless connection) to controller 1250 and/or the one or more sensors, to capture, display, and/or record pump operating parameters such as speed, blood flow rate, power usage and remaining battery life. Console data may be exported for analysis and confirmation of historical operating parameters for the system.

An interface board can serve as a communication hub between the system controller and a physician control interface 1256. The physician control interface 1256 can be used by a physician or other healthcare provider to manage and monitor the pump speed and settings.

The control interface may include a graphical user interface (GUI) and may also include its own independent power source. The control interface may take the form factor of computer tablet running software that includes the GUI, and the interface can capture, display, and record pump operating parameters such as speed, blood flow rate, power usage, and remaining battery life. The control interface may display pump operating parameters and allow for monitoring and adjustment of pump parameters by the physician or clinical team. In some embodiments, parameters such as flow rate and information from sensors and pump can be sent to the controller for wireless streaming data transmission, and as a result may be accessed by a secure web-based access system in real-time.

In some embodiments, the cartridge, front bearing mount/flow straightener, impeller, and diffuser can be machined and polished from a suitable medical-grade material such as titanium or a titanium alloy (e.g. grade 23 titanium). The internal bearings that support the rotational motion of the impeller can be made from a bearing material such as silicon carbide and/or zirconia ceramic for long term application or a polymer/composite with sufficient wear properties for short term applications. In some embodiments, one or more of the cartridge, front bearing mount/flow straightener, impeller, and diffuser can be formed from a material such as a polymer or other metal, and then be coated with a suitable biocompatible bearing material. Such an arrangement may permit components to be in direct contact with one another without the need for separate bearing structures. For example, one or more of these components may be injection molded with a polymer, followed by machining of a bearing surface into the molded component, followed by coating the component with a ceramic material.

Figure 14:
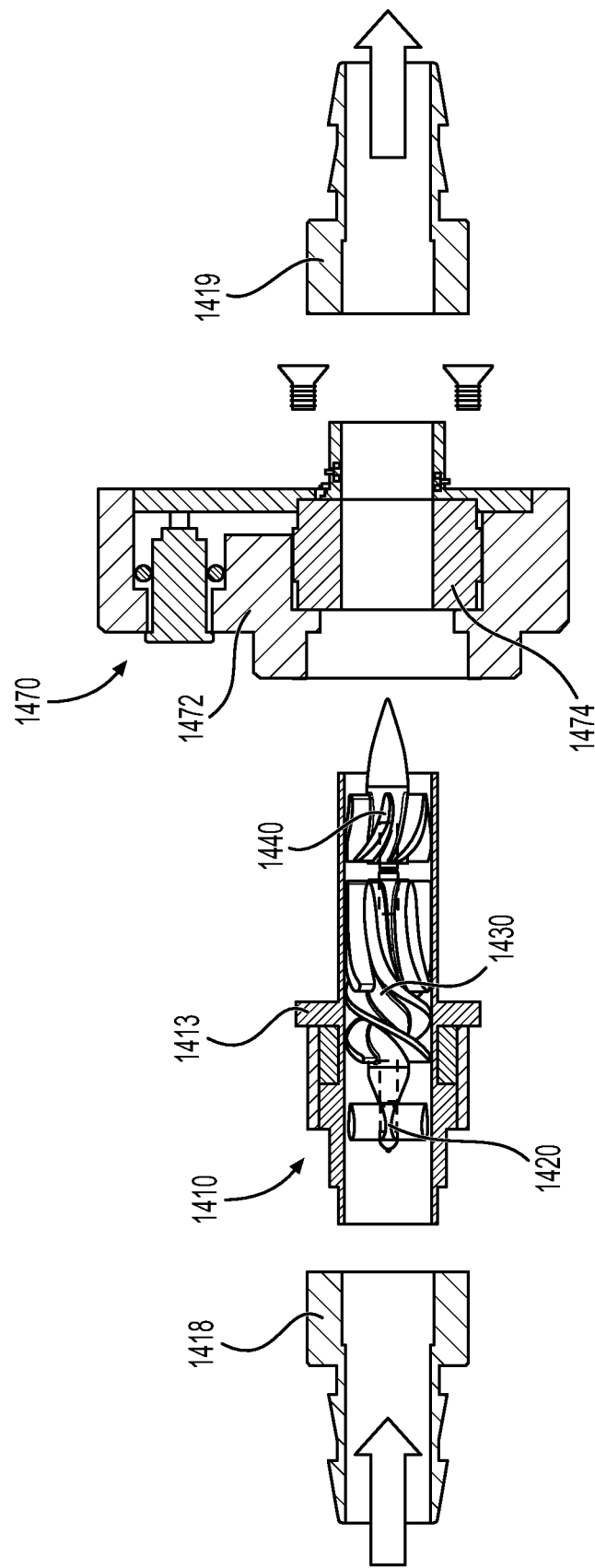
FIG. 14 an exploded cross-sectional view of a pump assembly configured for extracorporeal application, according to aspects of this disclosure.

FIG. 14 an exploded cross-sectional view of a pump assembly 1400 configured for extracorporeal application, according to aspects of this disclosure;

The extracorporeal blood pump system of FIG. 14 can include a disposable blood pump cartridge, which includes pump housing 1410 and the internal blood contacting components (e.g., flow straightener 1420, impeller 1430, and diffuser 1440), in combination with a reusable stator 1470. The disposable components can be connected to the patient via cannulation and tubing as required for the specific clinical therapy being utilized. For example, inlet adapter 1418 and outlet adapter 1419 may be barbed tubing connectors. This blood circuit could include oxygenation systems or other systems for extraction or infusion of other therapeutic constituents of the blood flow. In some embodiments, the pump cartridge may contain permanent magnet(s) to externally couple with the reusable stator 1470. As discussed above, stator 1470 provides the electromagnetic forces to rotate impeller 1430 and operate the pump mechanism.

Figure 15A:
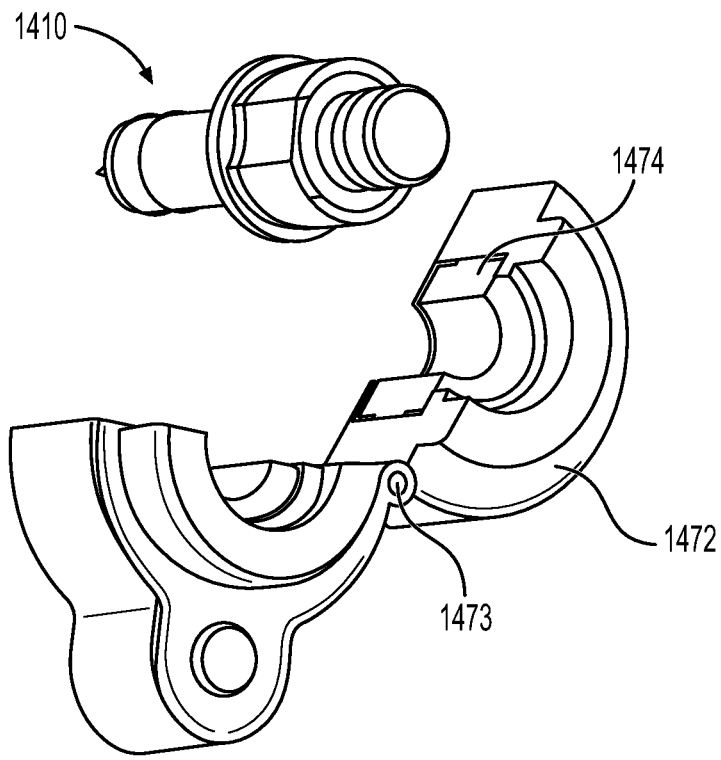
FIGS. 15A and 15B are perspective views of a stator cartridge in open and closed states, respectively, according to aspects of this disclosure.
Figure 15B:
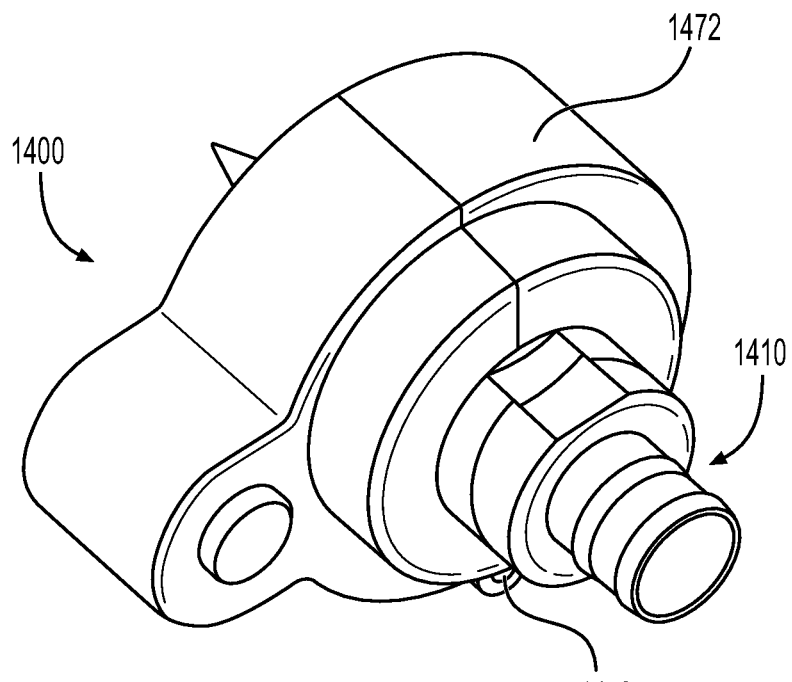

FIGS. 15A and 15B are perspective views of an embodiment of reusable stator 1470 in open and closed states, respectively. To provide more flexibility with installation, assembly, and maintenance, stator 1470 may also be capable of being clipped or otherwise assembled on the outside of pump housing 1410. This manner of external attachment can aid in the bypass system assembly by allowing the stator 1470 to be selectively engaged with pump housing 1410 before or after pump assembly 100 has been connected to the circulatory system of the patient. This selective engagement without the requirement that pump housing 1410 be uncoupled can allow sterility to be maintained through the coupling and uncoupling of stator 1470.

Reusable stator 1470 can include stator housing 1472, stator core 1474, and a hinge 1473. Stator 1470 can employ a clamshell design to facilitate ease of insertion of pump housing 1410, particularly when it is connected to the patient. A portion of stator housing 1472 and stator core 1474, for example a semicircular portion, can be pivoted or otherwise articulated with respect to another portion of stator housing 1472 and stator core 1474 to an open position. The portions of stator core 1474 can be connected electrically using flexible wires which can bend with the assembly while it is hinged open, and/or can include electrical contacts which can disconnect when stator 1470 is opened and reconnect when stator 1470 is closed. To provide each coil of stator core 1474 with similar electrical characteristics, despite any additional wire length required to connect the stator halves, inline resistance may be added. In some embodiments, a controller for pump assembly 1400 may detect the state/position of stator 1470 using, for example, the back electromagnetic force (EMF) measured from the coils or by using separate sensors.

With stator 1470 in the open position, it may be positioned about pump housing 1410 and/or pump housing 1410 may be positioned inside of stator 1470. Stator 1470 may be aligned with an appropriate portion of pump housing 1410 and impeller 1430 through the use of physical and/or visual indicators. For example, in some embodiments, stator 1470 may be positioned to abut flanged portion 1413 when properly positioned, or flanged portion 1413 may fit within a cooperating recess in stator housing 1472.

Once the pump housing 1410 is inserted, stator 1470 be closed to form a circumferential ring about impeller 1430 as necessary to produce the rotating magnetic field that drives pump assembly 1400. A hinged stator 1470 can then be secured in place with suitable mechanical fasteners, such as screws, bolts, clips, clamps, or latches. In some embodiments, the stator cartridge is a unitary component that is slid onto, or otherwise removably affixed to, the cartridge prior to being connected to the patient's circulatory system.

In some embodiments, stator 1470 may be a brushless direct current (DC) stator and include an anodized aluminum stator housing 1472 with an iron inner core 1474. Because stator 1470 is not in direct contact with the blood flow, it may be able to be cleaned/autoclaved and reused.

Figure 16:
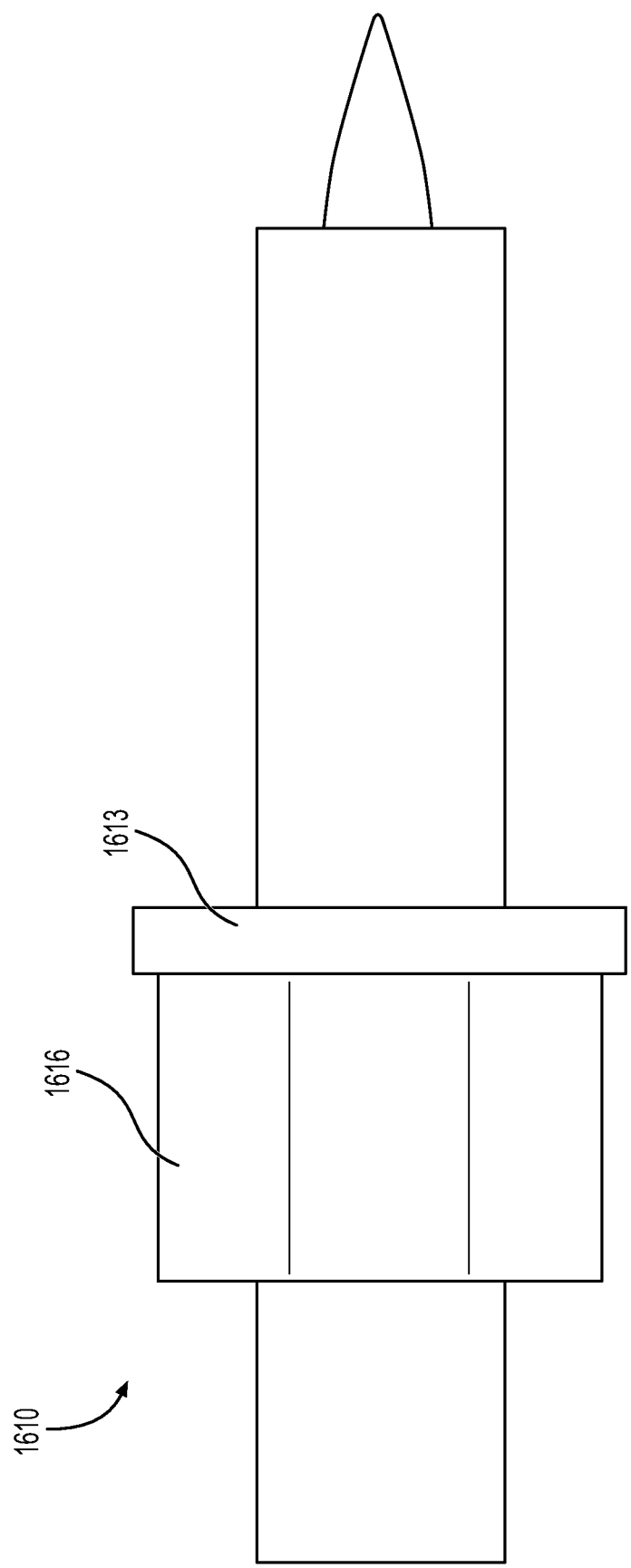
FIG. 16 is a side view of a pump assembly with a tube stretcher installed, according to aspects of this disclosure.
Figure 17:
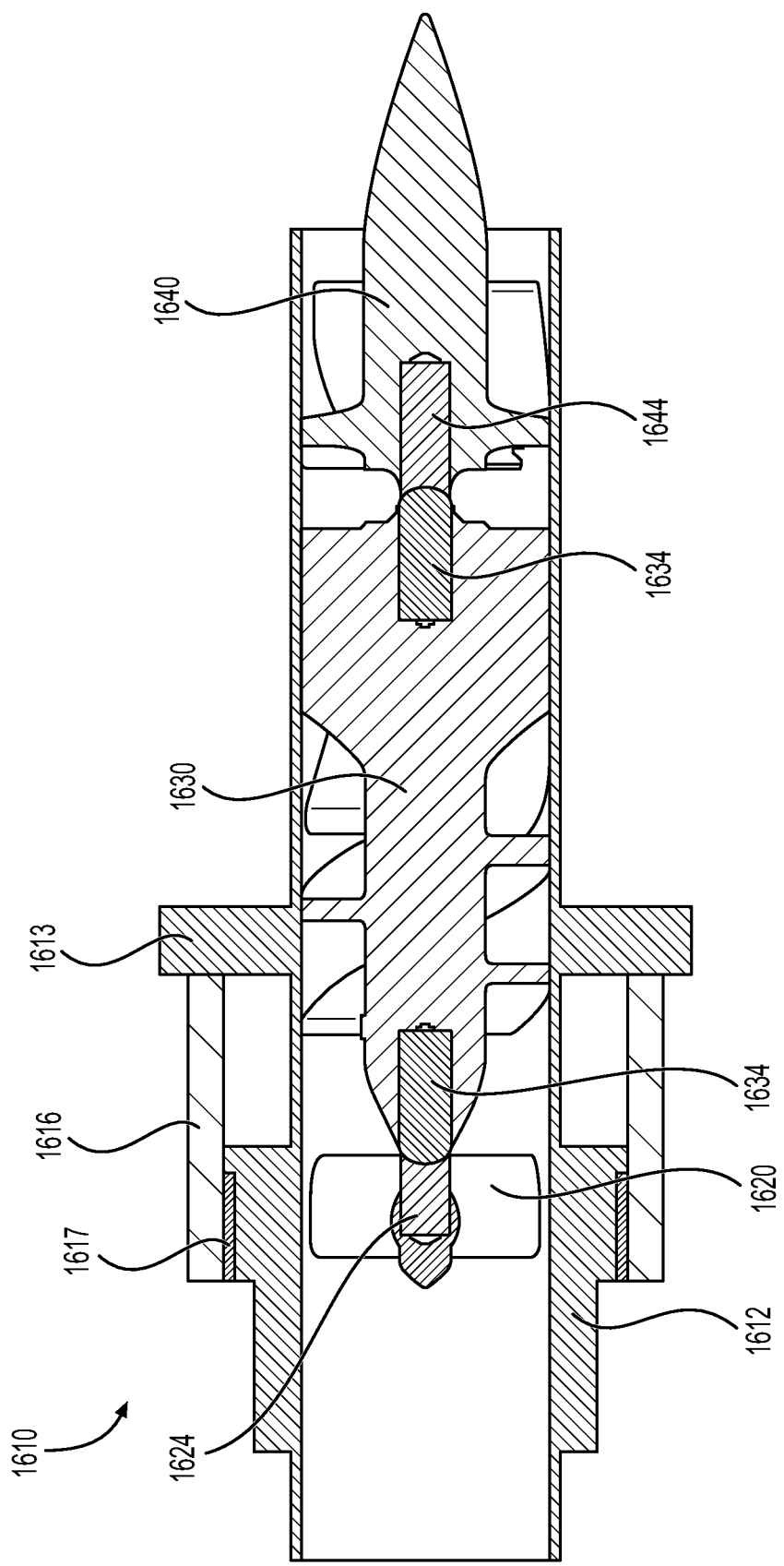
FIG. 17 is a cross-sectional view of the pump assembly with a tube stretcher installed of FIG. 16, according to aspects of this disclosure.

FIG. 16 is a side view of a pump assembly 1600 (including flow straightener 1620, impeller 1630, and diffuser 1640) with a tube stretcher 1616 installed, and FIG. 17 is a cross-sectional view of pump assembly 1600 with tube stretcher 1616 installed to enable more precise pump mechanism positioning within the pump cartridge. Tube stretcher 1616 can be an internally-threaded tube with a fine pitched thread 1617, such as 48 pitch thread, and can mesh with complementary threads on threaded portion 1612 of pump housing 1610. The fine threading of threaded portion 1612 and thread 1617 can provide for precise adjustments to achieve repeatable and exact operating clearance specification for the bearings. Tube stretcher 1616 may abut flanged portion 1613 (or another anchoring point), and may urge the threaded portion 1612 of pump housing 1610 towards flanged portion 1613 to create strain that is capable of modifying a dimension of the flow tube.

During flow tube manufacture and assembly, torque applied to tube stretcher 1616 can apply strain to pump housing 1610 sufficient to move flow straightener 1620, including bearing mount 1624, to a position spaced a particular distance from flanged portion 1613. This applied strain can maintain the proper gap to reduce friction and wear on bearing mounts 1624 and 1644 as well as bearings 1634 for smoother rotational motion of impeller 1630. Tube stretcher 1616 may maintain its positioning by the forces of friction between it and the threads and/or flange, or may be secured through other suitable methods such as an external locking mechanism. Gaps between the internal components may be in the range of about 0.0001 to about 0.001 inches (about 0.0025-0.025 mm), and tube stretcher 1616 can be able to adjust the spacing between mount 1624 and flanged portion 1613 by about 0.00005 to 0.0005 inches (about 0.00125-0.0125 mm). Tube stretcher 1616 may be made from a material such as stainless steel, and because tube stretcher 1616 may be an external component of the flow tube, it may not be blood-contacting.

Figure 18:
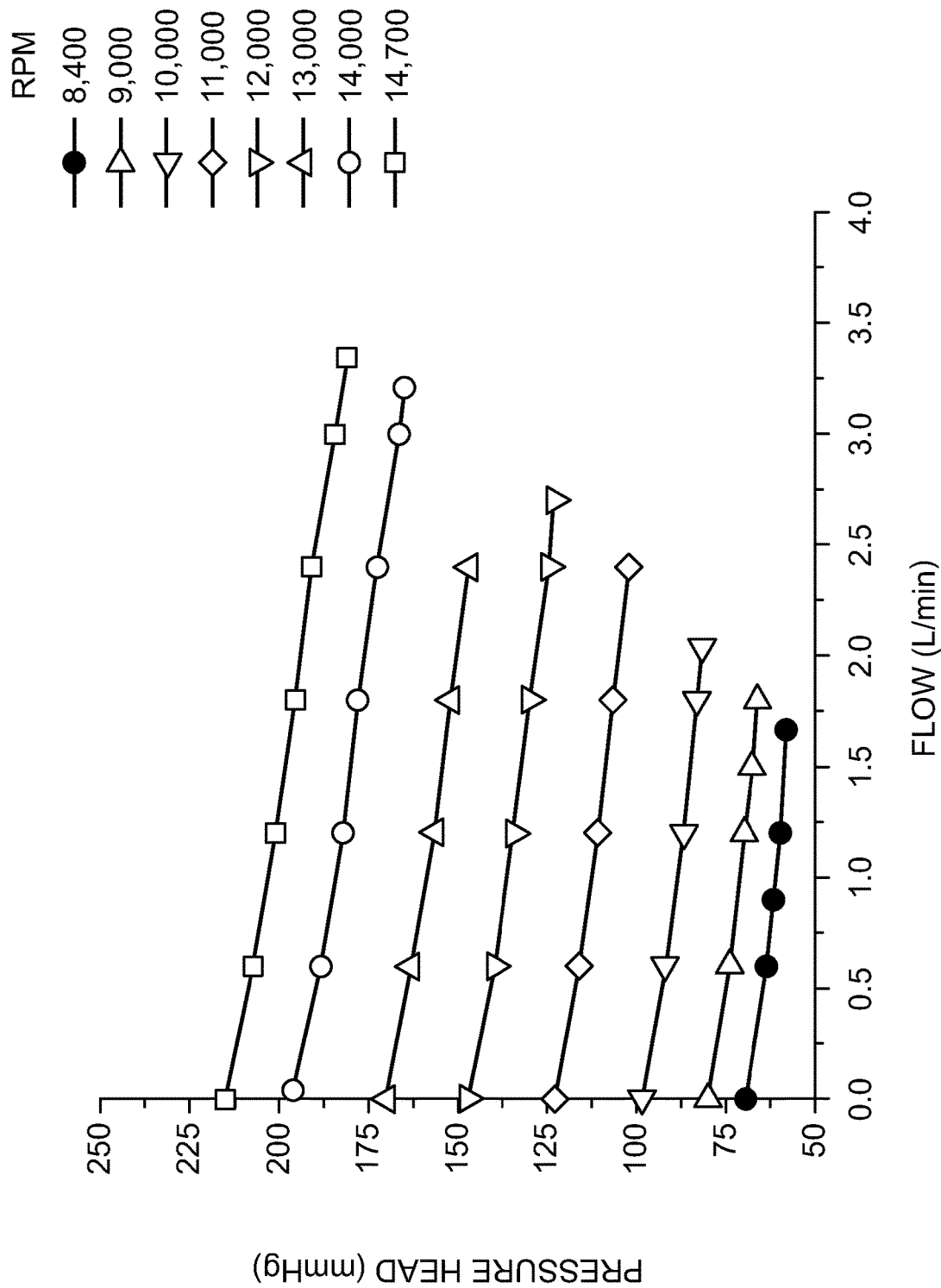
FIG. 18 is a plot of the head pressure ("H") produced by a pump according to an embodiment of this disclosure, as a function of flowrate ("Q") through the pump.

FIG. 18 is a plot of the head pressure ("H") produced by a pump assembly 100 according to an embodiment of this disclosure, as a function of flowrate ("Q") through the pump. In order to evaluate the pump performance, a pump curve may be plotted based on the pump design and pump speed. The pump curve may be characteristic to a particular pump design and geometry, and can be a plot of the head pressure ("H") produced by the pump as a function of flowrate ("Q") through the pump. The pump curve plotted in FIG. 18 demonstrates the performance of a pump according to an embodiment of this disclosure when incorporated, for example, in a cannula circuit as a bypass pump. The slope shown indicates that, for a given pump speed, the pressure head does not drop significantly as the flow rate increases. The plotted curve also shows that a pump assembly 100 in accordance with the present disclosure can achieve continued parallel incremental performance with speed as head pressure increases.

Figure 19:
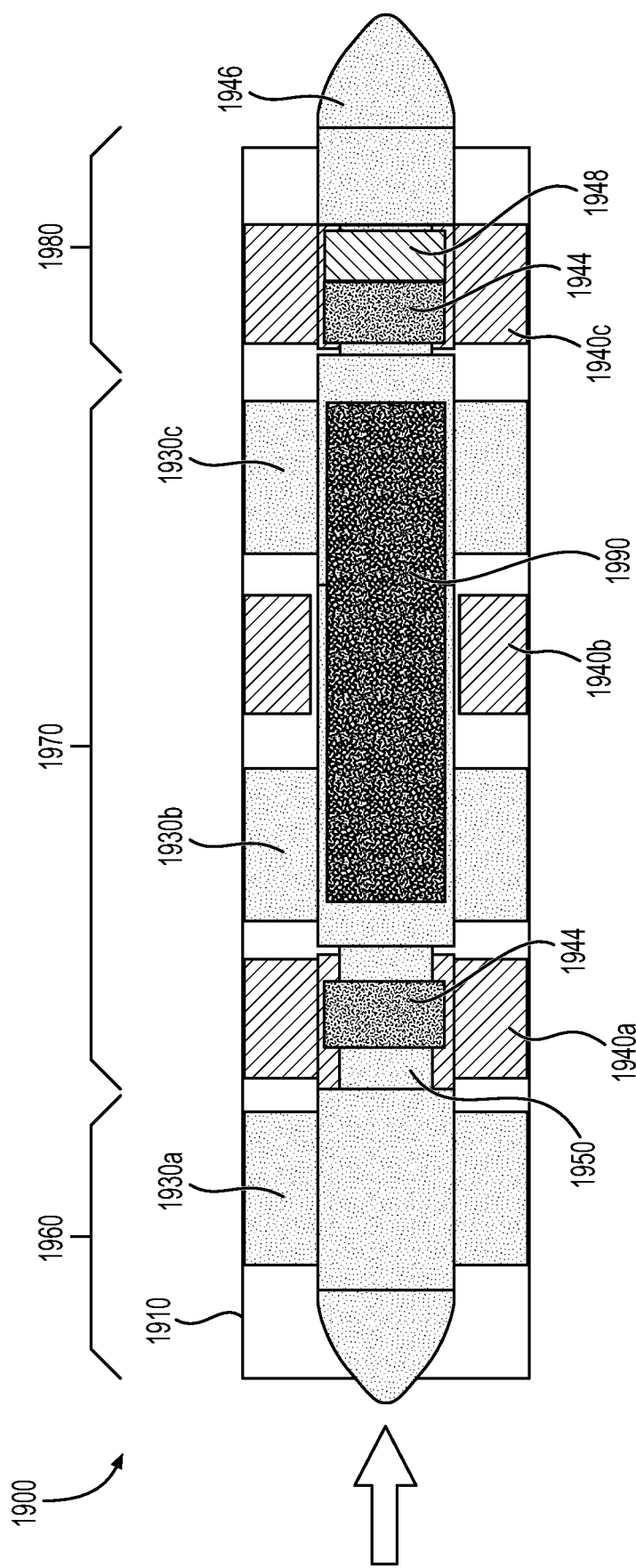
FIG. 19 is a schematic representation of a multistage pump assembly, according to aspects of this disclosure.

In some applications, higher pressure rises required (e.g., on the order of 150 mm Hg @ 4 lt/m) may call for a multi-stage impeller 130 element. A single-stage impeller 130 can yield its peak efficiency at about 4 lt/m flow rate around 9,500 rpm. In such an embodiment, a rotation speed of approximately 13,000 rpm would be required to achieve a pressure rise of approximately 150 mmHg. Because impeller speeds that are beyond the efficient range for a particular impeller design can cause flow issues, such as flow separation bubbles/cavitation, a multi-stage pump assembly 200 may be desired. FIG. 19 is a schematic representation of a multi-stage pump assembly 1900, according to aspects of this disclosure. Multi-stage pump assembly 1900 may be provided with multiple impellers 1930 and diffusers 1940 in series within the pump housing 1910 to achieve higher pressures and flows, while reducing the rotation speeds necessary. Impellers 1930 can be used in tandem, either stacked or in series, to provide flow to the pressure flow requirements for a particular perfusion application.

Multi-stage pump assembly 1900 may be able to deliver the required blood flow rate through a high-pressure oxygenation system. While normal arterial blood pressures can be in the range of about 60 mmHg to about 130 mmHg, the addition of an oxygenation system can require a pump capable of delivering flow against a pressure of about 300 mmHg or more.

Multi-stage pump assembly 1900 can include three impeller-diffuser stages to deliver the required blood flow rate in a high-pressure, patient oxygenation system. Blades may be designed to allow multiple impellers 1930 to be near their best efficiency while minimizing blood stress. For example, four impeller blades can be used in each of impellers 1930 and five diffuser fins can be used in each of diffusers 1940, with the impeller blades and diffuser fins having a similar design as discussed with respect to other embodiments disclosed. As with the single-stage impeller application, impellers 1930 and diffusers 1940 can be located on a single, rigid shaft 1950.

The shaft can consist of an upstream section 1960, a center section 1970, and a downstream section 1980, with the upstream section including the first impeller 1930a, and the center section including the remaining two impellers 1930b and 1930c. Reduced diameter connections between the shaft sections can allow for the use of journal bearings 1944 to support the shaft in the radial dimension. In some embodiments, the first and third diffusers 1940a and 1940c can be an integral part of journal bearings 1944, and can connect the journal bearings 1944 to the non-rotating outer housing 1910. Support for the shaft in the axial direction can be provided by thrust bearing components 1948 located in the third diffuser 1940c, and upstream of end cap 1946. In some embodiments, the second diffuser 1940b may not contain any bearings, provided journal bearings 1944 provide sufficient support. The second diffuser 1940b may be of a split-case design in that it has an axial passage therethrough and is only connected to pump housing 1910.

Connections between the shaft sections can be press fit, threaded, laser welded, or adhered with an adhesive, with the selection driven by considerations such as structural integrity, motor encapsulation, and other manufacturing requirements.

The rotating shaft of multi-stage pump assembly 1900 can be driven by electromagnetic forces between a permanent motor magnet 1990 located within shaft 1950 and a stator (not shown) located in or around pump housing 1910. Magnet 1990 may be a single permanent magnet for a two-pole motor design or may be a series of magnets or magnet quadrant sectors magnetized radially for a four-pole magnet design. As with the single-stage embodiments, a tube stretcher mechanism may be used on pump housing 1910 to ensure appropriate component alignment and spacing.

It will be apparent to those skilled in the art that various modifications and variations may be made in the disclosed systems and methods without departing from the scope of the disclosure. It should be appreciated that the disclosed systems may include various suitable computer systems and/or computing units incorporating a plurality of hardware components, such as, for example, a processor and non-transitory computer-readable medium, that allow the systems to perform one or more operations during a method in accordance with those described herein. Other aspects of the disclosure will be apparent to those skilled in the art from consideration of the specification and practice of the features disclosed herein. It is intended that the specification and examples be considered as exemplary only.

The pump assemblies and their various related components and peripherals may be programmed and/or controlled via any suitable components, including computing devices, hardware, software, and related peripherals or other components. This portion of the specification describes examples of such components. For example, the various pump systems may include any computing device. The computing device may include input and output ports to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of this disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of this disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It will be apparent to those skilled in the art that various modifications and variations can be made to the disclosed system, methods, and devices without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. An apparatus for pumping blood, the apparatus comprising:
   a pump housing having an outer wall radially disposed about a longitudinal pump axis, the pump housing having an upstream end and a downstream end;
   an impeller positioned between the upstream end and the downstream end within the pump housing, the impeller supported by an upstream bearing and a downstream bearing, wherein the impeller includes a permanent magnet; and
   a stator positioned circumferentially about the impeller and configured to impart a rotational motion to the impeller by applying a magnetic field to the permanent magnet of the impeller,
   wherein the stator includes a stator housing, a stator core, and a hinge,
   wherein a first semicircular portion of the stator housing and the stator core is pivotable, using the hinge, with respect to a second semicircular portion of the stator housing and the stator core, between an open position and a closed position, and
   wherein the stator includes one or more sensors configured to provide a signal indicating whether the stator is in the open position or the closed position.

2. The apparatus of claim 1, wherein the stator is a brushless, direct current stator.

3. The apparatus of claim 1, further comprising:
one or more mechanical fasteners to secure the stator in place on the pump housing.

4. The apparatus of claim 1, wherein the stator is configured to not be in direct contact with a blood flow of a patient when the apparatus is connected to a circulatory system of the patient.

5. The apparatus of claim 1,
wherein the stator is configured to be selectively coupled to the outer wall of the pump housing before or after the pump housing has been connected to a circulatory system of a patient.

6. The apparatus of claim 1, wherein the permanent magnet is a single, two-pole permanent magnet.

7. The apparatus of claim 6,
wherein the stator housing includes an aperture at a downstream end of the stator housing, and
wherein the aperture is configured to connect to a feed through to allow cables and wires that provide power and/or signals to the stator to pass through the stator housing.

8. The apparatus of claim 6, wherein the first semicircular portion of the stator housing and the stator core and the second semicircular portion of the stator housing and the stator core are connected electrically using flexible wires which bend between the open position and the closed position.

9. The apparatus of claim 6, wherein the first semicircular portion of the stator housing and the stator core and the second semicircular portion of the stator housing and the stator core are connected electrically using electrical contacts which disconnect when the stator is opened and connect when the stator is closed.

10. The apparatus of claim 1, further comprising:
one or more controllers configured to detect, using the signal from the one or more sensors, whether the stator is in the open position or the closed position.

11. The apparatus of claim 1, wherein the outer wall of the pump housing includes an externally facing engagement feature and a surface transverse to the longitudinal pump axis, and
wherein the stator includes a recess configured to abut the externally facing engagement feature of the outer wall of the pump housing to align the stator with the impeller.

12. An apparatus for pumping blood, the apparatus comprising:
a pump housing having an outer wall radially disposed about a longitudinal pump axis, the pump housing having an upstream end and a downstream end;
a front bearing mount positioned in the upstream end of the pump housing and secured to the pump housing;
a rear bearing mount positioned in the downstream end of the pump housing and secured to the pump housing;
an impeller having a plurality of helically wound blades and positioned between the front bearing mount and the rear bearing mount within the pump housing; and
a pump drive positioned circumferentially about the impeller and configured to impart a rotational motion to the impeller by applying a magnetic field to the impeller;
wherein the pump drive includes a stator having a clamshell design configured to move the stator between an open position and a closed position, and
wherein the stator includes one or more sensors configured to provide a signal indicating whether the stator is in the open position or the closed position.

13. The apparatus of claim 12, further comprising:
one or more controllers configured to detect, based on the signal from the one or more sensors, whether the stator is open or closed.

* * * * *